(12) United States Patent
Nozaki

(10) Patent No.: US 7,239,735 B2
(45) Date of Patent: Jul. 3, 2007

(54) PATTERN INSPECTION METHOD AND PATTERN INSPECTION DEVICE

(75) Inventor: Takeo Nozaki, Tokyo (JP)

(73) Assignee: NEC Corporation (JP)

( * ) Notice: Subject to any disclaimer, the term of this patent is extended or adjusted under 35 U.S.C. 154(b) by 757 days.

(21) Appl. No.: 09/735,840

(22) Filed: Dec. 13, 2000

(65) Prior Publication Data

US 2001/0055415 A1 Dec. 27, 2001

(30) Foreign Application Priority Data

Dec. 16, 1999 (JP) .................................. 11-357273

(51) Int. Cl.
| | |
|---|---|
| G06K 9/00 | (2006.01) |
| G01N 37/00 | (2006.01) |
| G06F 19/00 | (2006.01) |
| G01C 17/38 | (2006.01) |
| G01P 21/00 | (2006.01) |
| G06K 9/40 | (2006.01) |
| G06F 15/00 | (2006.01) |
| H03F 1/26 | (2006.01) |
| H04B 15/00 | (2006.01) |

(52) U.S. Cl. .................. 382/141; 382/144; 382/145; 382/266; 702/81; 702/94; 702/190

(58) Field of Classification Search ........ 382/141–152, 382/266; 702/94–95, 81–84, 190–194
See application file for complete search history.

(56) References Cited

U.S. PATENT DOCUMENTS

| | | | | |
|---|---|---|---|---|
| 4,559,603 A | * | 12/1985 | Yoshikawa ..................... | 716/5 |
| 4,846,577 A | * | 7/1989 | Grindon ....................... | 356/610 |
| 4,962,541 A | * | 10/1990 | Doi et al. ..................... | 382/144 |
| 5,016,191 A | * | 5/1991 | Radochonski ............... | 345/596 |
| 5,237,650 A | * | 8/1993 | Priem et al. ................. | 345/443 |
| 5,726,443 A | * | 3/1998 | Immega et al. ........... | 250/227.2 |
| 5,917,934 A | * | 6/1999 | Chiu et al. .................. | 382/149 |

(Continued)

FOREIGN PATENT DOCUMENTS

EP   0105661   4/1984

(Continued)

OTHER PUBLICATIONS

Li et al. "Subpixel edge detection and estimation with a microprocessor-controlled line scan camera." IEEE Transactions on Industrial Electronics, vol. 35, No. 1, Feb. 1998, pp. 105-112.*

(Continued)

Primary Examiner—Bhavesh M Mehta
Assistant Examiner—Manav Seth
(74) Attorney, Agent, or Firm—Dickstein, Shapiro, LLP.

(57) ABSTRACT

In this pattern inspection device, the optical scanning section scans the inspected pattern using a laser beam. A photoelectric image processing section generates an image of the inspected pattern. A reference image generation section calculates the gray level of each pixel according to the number of sub-pixels belonging to the pattern developed in each pixel and calculates the pattern width for the inspected pattern and the reference data with treating the count obtained by dividing the gray level by the gray level step count as the width of the pattern developed in that pixel.

9 Claims, 14 Drawing Sheets

U.S. PATENT DOCUMENTS

| | | | |
|---|---|---|---|
| 6,040,911 A * | 3/2000 | Nozaki et al. | 356/394 |
| 6,071,652 A * | 6/2000 | Feldman et al. | 430/5 |
| 6,076,465 A * | 6/2000 | Vacca et al. | 101/481 |
| 6,356,300 B1 * | 3/2002 | Shiba | 348/130 |
| 6,504,947 B1 * | 1/2003 | Nozaki et al. | 382/148 |
| 6,583,897 B1 * | 6/2003 | Harrington | 358/532 |

FOREIGN PATENT DOCUMENTS

| | | | |
|---|---|---|---|
| EP | 0899559 | | 3/1999 |
| EP | 0930499 | | 7/1999 |
| EP | 0952548 | | 10/1999 |
| JP | 55150667 | A * | 11/1980 |
| JP | 4-181105 | | 6/1992 |
| JP | 04-350776 | | 12/1992 |
| JP | 11-205823 | | 7/1999 |
| JP | 11-304453 | | 11/1999 |

OTHER PUBLICATIONS

Reference material: Yoshihiko Nomura et al. Sub-pixel Expression of Edge Position Measurement and Error Analysis, Electronic Information Communication Association Paper, D-11, vol. J73-D-11, No. 9, pp. 1458-1467, Sep. 1990—in Specification, p. 4.

Japanese Office Action issued Jun. 24, 2003 (w/ English translation of relevant portion).

* cited by examiner

| 0 | 0 | 0 | 0 | 0 | 0 | 0 |
|---|---|---|---|---|---|---|
| 128 | 128 | 128 | 128 | 96 | 0 | 0 |
| 255 | 255 | 255 | 255 | 192 | 0 | 0 |
| 255 | 255 | 255 | 255 | 192 | 0 | 0 |
| 255 | 255 | 255 | 255 | 192 | 0 | 0 |
| 255 | 255 | 255 | 255 | 192 | 0 | 0 |

22

PIXEL OF PATTERN EDGE POSITION AT LEFT END
WIDTH OF A PIXEL
PIXEL OF PATTERN EDGE POSITION AT RIGHT END
21
22
COMPLETE PIXELS
22

FIG. 12

| X\Y | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|
| 190 | | 0 | 0 | 0 | 0 | 0 | 0 | 0 | 0 | 0 | 0 | 0 | 0 | 0 | 0 | 0 | 0 | 0 | 0 | 0 | 0 |
| 189 | | 0 | 0 | 0 | 0 | 0 | 0 | 0 | 0 | 0 | 0 | 0 | 0 | 0 | 0 | 0 | 0 | 0 | 0 | 0 | 0 |
| 188 | | 0 | 0 | 0 | 0 | 0 | 0 | 0 | 0 | 0 | 0 | 0 | 0 | 0 | 0 | 0 | 0 | 0 | 0 | 0 | 0 |
| 187 | | 0 | 0 | 0 | 0 | 0 | 0 | 0 | 0 | 0 | 0 | 0 | 0 | 0 | 0 | 0 | 0 | 0 | 0 | 0 | 0 |
| 186 | | 0 | 0 | 0 | 0 | 0 | 0 | 0 | 0 | 0 | 0 | 0 | 0 | 0 | 0 | 0 | 0 | 0 | 0 | 0 | |
| 185 | | 0 | 0 | 0 | 0 | 0 | 0 | 0 | 0 | 0 | 0 | 0 | 0 | 0 | 0 | 0 | 0 | 0 | 0 | 0 | |
| 184 | | 2 | 2 | 2 | 2 | 2 | 2 | 2 | 2 | 2 | 2 | 2 | 2 | 2 | 2 | 2 | 2 | 2 | 2 | 2 | 2 |
| 183 | | 84 | 84 | 84 | 84 | 84 | 84 | 84 | 84 | 84 | 84 | 84 | 84 | 84 | 84 | 84 | 84 | 84 | 84 | 84 | 84 |
| 182 | | 198 | 198 | 198 | 198 | 198 | 198 | 198 | 198 | 198 | 198 | 198 | 198 | 198 | 198 | 198 | 198 | 198 | 198 | 198 | 198 |
| 181 | | 255 | 255 | 255 | 255 | 255 | 255 | 255 | 255 | 255 | 255 | 255 | 255 | 255 | 255 | 255 | 255 | 255 | 255 | 255 | 255 |
| 180 | | 255 | 255 | 255 | 255 | 255 | 255 | 255 | 255 | 255 | 255 | 255 | 255 | 255 | 255 | 255 | 255 | 255 | 255 | 255 | 255 |
| 179 | | 255 | 255 | 255 | 255 | 255 | 255 | 255 | 255 | 255 | 255 | 255 | 255 | 255 | 255 | 255 | 255 | 255 | 255 | 255 | 255 |
| 178 | | 255 | 255 | 255 | 255 | 255 | 255 | 255 | 255 | 255 | 255 | 255 | 255 | 255 | 255 | 255 | 255 | 255 | 255 | 255 | 255 |
| 177 | | 228 | 228 | 228 | 228 | 228 | 228 | 228 | 228 | 228 | 228 | 228 | 228 | 228 | 228 | 228 | 228 | 228 | 228 | 228 | 228 |
| 176 | | 135 | 135 | 135 | 135 | 135 | 135 | 135 | 135 | 135 | 135 | 135 | 135 | 135 | 135 | 135 | 135 | 135 | 135 | 135 | |
| 175 | | 39 | 39 | 39 | 39 | 39 | 39 | 39 | 39 | 39 | 39 | 39 | 39 | 39 | 39 | 39 | 39 | 39 | 39 | 39 | |
| 174 | | 0 | 0 | 0 | 0 | 0 | 0 | 0 | 0 | 0 | 0 | 0 | 0 | 0 | 0 | 0 | 0 | 0 | 0 | 0 | |
| 173 | | 0 | 0 | 0 | 0 | 0 | 0 | 0 | 0 | 0 | 0 | 0 | 0 | 0 | 0 | 0 | 0 | 0 | 0 | 0 | |
| 172 | | 0 | 0 | 0 | 0 | 0 | 0 | 0 | 0 | 0 | 0 | 0 | 0 | 0 | 0 | 0 | 0 | 0 | 0 | 0 | 0 |
| 171 | | 0 | 0 | 0 | 0 | 0 | 0 | 0 | 0 | 0 | 0 | 0 | 0 | 0 | 0 | 0 | 0 | 0 | 0 | 0 | |
| 170 | | 0 | 0 | 0 | 0 | 0 | 0 | 0 | 0 | 0 | 0 | 0 | 0 | 0 | 0 | 0 | 0 | 0 | 0 | 0 | 0 |

FIG.14

| | | | | | | |
|---|---|---|---|---|---|---|
| 0, | 0, | 0. | 0, | 0, | 0, | 0, |
| 0, | 0, | 28, | 118, | 15, | 0, | 0, |
| 0, | 0, | 198, | 255, | 144, | 0, | 0, |
| 0, | 0, | 254, | 255, | 188, | 0, | 0, |
| 0, | 0, | 198, | 255, | 144, | 0, | 0, |
| 0, | 0, | 28, | 118, | 15, | 0, | 0, |
| 0, | 0, | 0, | 0, | 0, | 0, | 0, |

PATTERN INSPECTION METHOD AND PATTERN INSPECTION DEVICE

BACKGROUNDS OF THE INVENTION

1. Field of the Invention

The present invention relates to a pattern inspection device and particularly relates to a pattern inspection method and a pattern inspection device characterized by its reference image preparation procedure to prepare the reference image for Die-To-Data Base Inspection from the design data.

2. Description of the Related Art

It is generally necessary to inspect fine patterns of the semiconductor integrated circuit or the like formed on the photo-mask, reticle or wafer liquid crystal using a pattern inspection device to see whether they are correctly drawn according to the dimensions and shapes of the ideal pattern prepared from the design data.

In this type of pattern inspection device, the design data given with square or trapezoid position coordinates and line length are expressed as binary bit string consisting of 0 and 1 corresponding to the inspected pattern. Density values in a pixel are generated by integration of the bit string within the pixel width of a predetermined resolution.

Next, a certain optical point spread function is prepared based on the pattern information obtained by scanning the inspected pattern with the laser beam and making an image on the light receiving device with the light which has passed the pattern or based on the edge profiling of the pattern image obtained from the image sensing system. Using this function and executing the convolution operation with the multiple gray scale data (multi-value data) in the design data, the reference image is obtained.

Defects on the inspected pattern are detected by reading the reference image obtained from the design data synchronizing with the image of the inspected pattern obtained by optical scanning or by input from the image sensing system and by finding discrepancies between the image of the inspected pattern and the reference image at corresponding pixel positions (Die-To-Data BASE inspection).

Under the optical conditions and influence of the manufacturing processes, the image of the inspected pattern has thicker or thinner line widths and other dimensional errors when compared with the ideal design values. Pseudo discrepancies from the reference image obtained from the design data tend to result in pseudo defects, which should not be judged as defects.

Therefore, it is necessary to execute appropriate characteristics extraction such as edge position detection corresponding to the characteristics amount in each inspection zone and to correct in advance the pattern width of the multiple gray scale image in the design data before convolution processing with the optical point spread function so that such width comes to the edge position of the image in the inspected pattern.

In the conventional reference image preparation method, when correcting the pattern width of the reference image, the inspected pattern image is subjected to an appropriate edge detection processing so that the pattern correction width in the design data are used for correction as it is, i.e. the binary data by the unit of bits (pixel).

In this case, by preparing the change bit pattern from the design bit pattern and obtaining its EX-OR with the bit data of the inspected pattern as the binary expression of the actual image, the pattern of the reference image is resized.

In addition, for edges and corners extracted from the design data by edge position detection and corner recognition, corrective templates by the unit of bits expressing an edge or corner of a certain pattern edge angle (0, 45, 90 and 135 deg. for example) are prepared.

Then, the correction template the most similar to the actual image of the edges and corners is selected for correction of the original design data. The corrected design data are formed into multi-value data again for reference image preparation. Defects are detected by judging whether the gray scale difference between the obtained reference image and the actual image is defective or not using the threshold of a proper defect algorithm (Refer to Japanese Patent Application Laid-Open No. 350776/1992, for example).

Conventionally, image processing methods have been often used to detect the edge position of the inspected pattern. Such methods using image processing can be largely classified into density methods, methods using primary differentiation of density and methods using secondary differentiation of density (Reference material: Yoshihiko Nomura et al. "Sub-pixel Expression of Edge Position Measurement And Error Analysis". (Electronic Information Communication Association Paper D-11 Vol. J73-D-11 No. 9 pp. 1458–1467, September 1990).

According to a density method, a virtual edge pattern which can be applied the most suitably to the original image is determined for the primary to the third density moment so as to detect the edge position.

Density methods with primary differentiation include the method to consider the gravity center of the primary differentiation for all pixels forming the edge to be the edge position, the method to apply the primary differentiation of three consecutive pixels near the peak to the parabola so that the peak of the obtained regression curve is considered the edge position, and the method to apply the primary differentiation of density to the normal distribution by regression with least squares so that the extreme position of the regressive curve is considered the edge position. In the method using secondary differentiation of density, the secondary differentiation is determined using a special filter and the zero-cross position when the secondary differentiation result of two adjacent pixels with their positive and negative values transferred are linearly interpolated is considered to be the edge position.

A fine pattern drawn on the substrate such as photo mask has a zone of only about three pixels for transition from the black pixel level to the white pixel level at the pattern edge section and the edge profile is quite sharp. For this reason, when using the edge position detection method according to the conventional image processing, there is a drawback that a high level calculation is required even if the edge extraction algorithm by the unit of pixels or sub-pixels is used. Another drawback is that it takes a long time for calculation to identify the edge position by the unit of sub-pixels.

Further, in the conventional reference image preparation method, the relation between the optical point spread function corresponding to the beam spot strength including the machine system and the pattern edge position is not clear. Since the edge measurement position by the optical system and the edge extraction position by the image processing do not coincide, the pattern width of the inspected pattern and the pattern correction width of the reference data cannot be determined correctly.

SUMMARY OF THE INVENTION

The present invention has been made to solve the above problems. It is an object of the present invention to provide a reference image preparation method and a pattern inspection device which enable detection of the edge position in the inspected pattern by the unit of sub-pixels at a higher speed than the conventional method.

It is another object of the present invention to provide a reference image preparation method and a pattern inspection device which enable correct determination of the pattern width of the inspected pattern and the pattern correction width of the reference data and thereby enable achieving a reference image quite similar to the inspected pattern image.

According to the first aspect of the invention, a pattern inspection method which scans the inspected pattern formed on a substrate according to the design data and receives the light passing through the substrate with the light receiving device and, from the pattern information obtained by the light receiving device, generates the image of the inspected pattern and, for coincidence between this image and the reference data obtained by imaging of the design data, corrects the reference data to generate the reference image and compares the image of the inspected pattern and the reference image to detect any defects of the inspected pattern wherein the reference image generation being executed by determination of the edge boundary condition showing the gray level corresponding to the pattern edge position through convolution operation of the optical point spread function corresponding to the laser beam strength and the inspected pattern image as well as detection according to the edge boundary condition of the edge position in the inspected pattern by the unit of sub-pixels.

According to the second aspect of the invention, a pattern inspection method which scans the inspected pattern formed on a substrate according to the design data and receives the light passed through the substrate with the light receiving device and, from the pattern information obtained by the light receiving device, generates the image of the inspected pattern and, for coincidence between this image and the reference data obtained by imaging of the design data, corrects the reference data to generate the reference image and compares the image of the inspected pattern and the reference image to detect any defects of the inspected pattern wherein the reference image generation comprising provision to each pixel of sub-pixels dividing the pixel to form a matrix and calculation of the gray level of the pixel based on the number of sub-pixels belonging to the pattern developed in each pixel and calculation of the pattern width for the inspected pattern and for the reference data at the position at the corresponding position by treating the number obtained by dividing the gray level by the gray level step count as the width of the pattern developed in that pixel.

In the preferred construction, the gray level of each pixel is calculated from the number of sub-pixels belonging to the inspected pattern and, treating the count obtained by dividing this gray level by the gray level step count as the pattern width of the inspected pattern developed in the pixel, the pattern width of the inspected pattern is calculated and the gray level of each pixel is calculated from the number of sub-pixels belonging to the reference data pattern and, treating the count obtained by dividing this gray level by the gray level step count as the pattern width of the reference data developed in the pixel, the pattern width of the reference data is calculated.

In another preferred construction, the pattern correction width of the reference data is calculated from the difference between the pattern width of the inspected pattern and the pattern width of the reference data.

According to the third aspect of the invention, a pattern inspection device comprises a scanning means which scans the inspected pattern formed on the substrate according to the design data and receives the light passing through the substrate with the light receiving device, a photoelectric image processing means which generates the image of the inspected pattern from the pattern information obtained by the light receiving device in the scanning means, a reference image generation means which generates the reference image with correcting the reference data so that the positions of the image of the inspected pattern and the reference data obtained by imaging of the design data coincide, a comparison means which compares the image of the inspected pattern and the reference image to detect any defect in the inspected pattern, and an edge position detection means which determines the edge boundary condition showing the gray level corresponding to the pattern edge position through convolution operation of the optical point spread function corresponding to the laser beam strength and the image of the inspected pattern and detects the edge position of the inspected pattern by the unit of sub-pixels according to the edge boundary condition.

According to the fourth aspect of the invention, a pattern inspection device comprises a scanning means which scans the inspected pattern formed on the substrate according to the design data and receives the light passing through the substrate with the light receiving device, a photoelectric image processing means which generates the image of the inspected pattern from the pattern information obtained by the light receiving device in the scanning means, a reference image generation means which generates the reference image with correcting the reference data so that the positions of the image of the inspected pattern and the reference data obtained by imaging of the design data coincide, a comparison means which compares the image of the inspected pattern and the reference image to detect any defect in the inspected pattern, and a pattern width calculation means which provides each pixel with sub-pixels dividing the pixel into a matrix and calculates the gray level of each pixel based on the number of sub-pixels belonging to the pattern developed in each pixel and, with treating the count obtained by dividing this gray level by the gray level step count as the width of the pattern developed in the pixel, calculates the pattern width of the inspected pattern and the pattern width of the reference data at the corresponding position respectively.

In the preferred construction, the pattern width calculation means calculates the gray level of each pixel from the number of sub-pixels belonging to the inspected pattern and, with treating the count obtained by dividing this gray level by the gray level step count as the pattern width of the inspected pattern developed in the pixel, calculate the pattern width of the inspected pattern, and also calculates the gray level of each pixel from the number of sub-pixels belonging to the pattern of the reference data and, with treating the count obtained by dividing this gray level by the gray level step count as the pattern width of the reference data developed in the pixel, calculates the pattern width of the reference data.

In another preferred construction, the pattern width calculation means calculates the pattern correction width from the difference between the pattern width of the inspected pattern and the pattern width of the reference data.

According to the fifth aspect of the invention, a computer readable memory storing a pattern inspection program which, by controlling the computer, scans the inspected pattern formed on the substrate according to the design data with the laser beam and receives the light passing through the substrate with the light receiving device and generates the image of the inspected pattern according to the pattern information received by the light receiving device and, for coincidence of this image and the reference data position obtained by imaging of the design data, corrects the reference data to generate the reference data and compares the image of the inspected pattern and the reference image to detect any defect in the inspected pattern wherein the pattern inspection program executes, in the reference image generation process, determination of the edge boundary condition showing the gray level corresponding to the pattern edge position by convolution operation of the optical point spread function corresponding to the laser beam strength and the image of the inspected pattern and detection of the edge position of the inspected pattern by the unit of sub-pixels according to the edge boundary condition.

According to another aspect of the invention, a computer readable memory storing a pattern inspection program which, by controlling the computer, scans the inspected pattern formed on the substrate according to the design data using the laser beam, receives the light passing from the substrate with the light receiving device, generates the image of the inspected pattern based on the pattern information obtained by the light receiving device and, for position coincidence between this image and the reference data obtained by imaging of the design data, corrects the reference data and generates the reference image, and compares the image of the inspected pattern and the reference image to detect defects of the inspected pattern wherein the pattern inspection program executes, in the reference image generation, provision of sub-pixels dividing the pixel as a matrix to each pixel and calculation of the gray level for each pixel based on the number of sub-pixels belonging to the pattern developed in each pixel an calculation of the pattern width of the inspected pattern and the pattern width of the reference data at the corresponding position respectively with treating the count obtained by dividing the gray level by the gray level step count as the width of the pattern developed in the pixel.

Other objects, features and advantages of the present invention will become clear from the detailed description given herebelow.

BRIEF DESCRIPTION OF THE DRAWINGS

The present invention will be understood more fully from the detailed description given herebelow and from the accompanying drawings of the preferred embodiment of the invention, which, however, should not be taken to be limitative to the invention, but are for explanation and understanding only.

In the drawings:

FIG. 12 is an explanatory view to show the gray level distribution of the actual pattern at the position corresponding to the reference data of FIG. 11;

FIG. 14 is an explanatory view showing 7×7 optical point spread function;

DESCRIPTION OF THE PREFERRED EMBODIMENT

The preferred embodiment of the present invention will be discussed hereinafter in detail with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to unnecessary obscure the present invention.

First Embodiment

Figure 1:
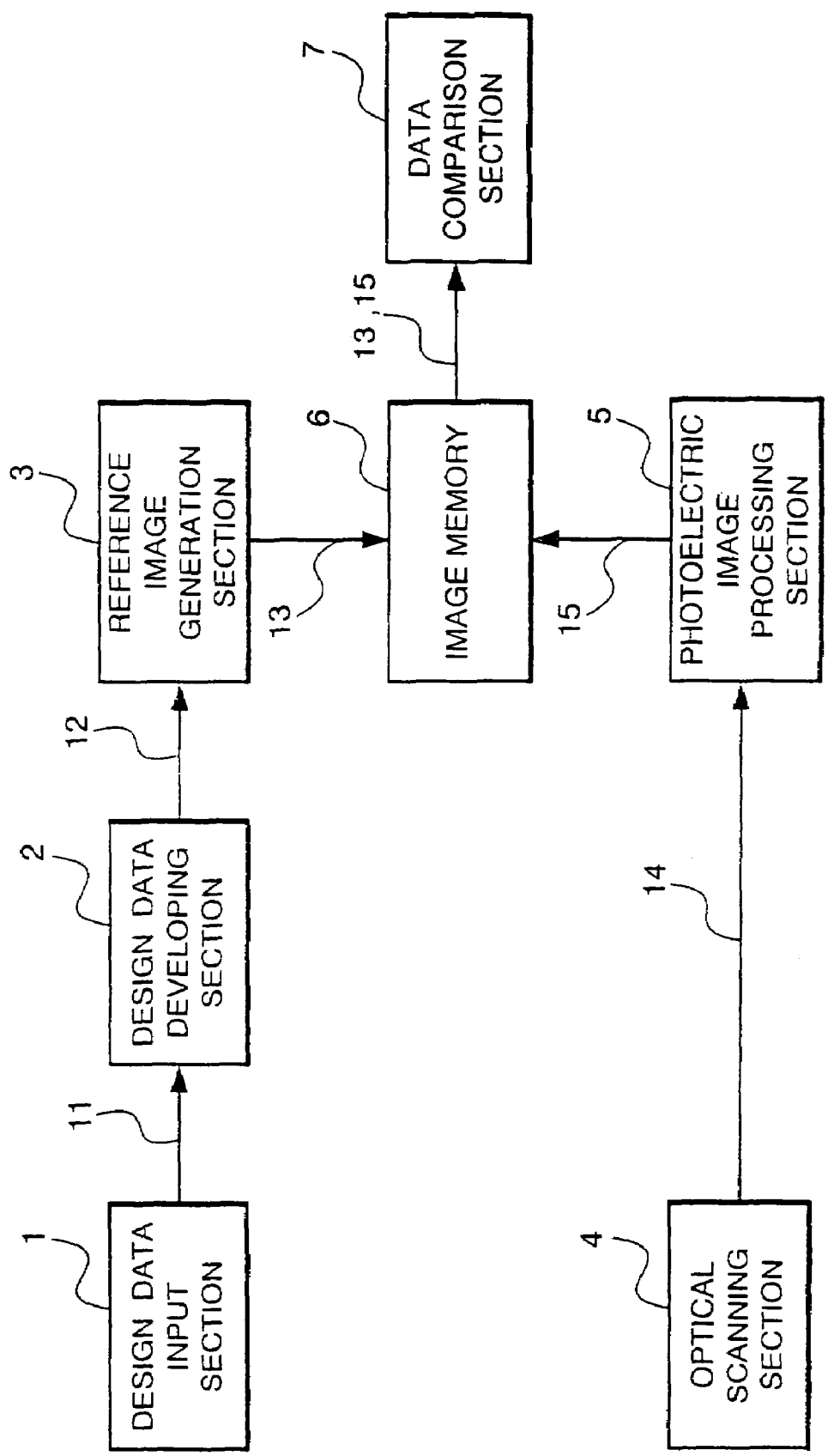
FIG. 1 is a block diagram of a pattern inspection device according to a first embodiment of the present invention.
Figure 2:
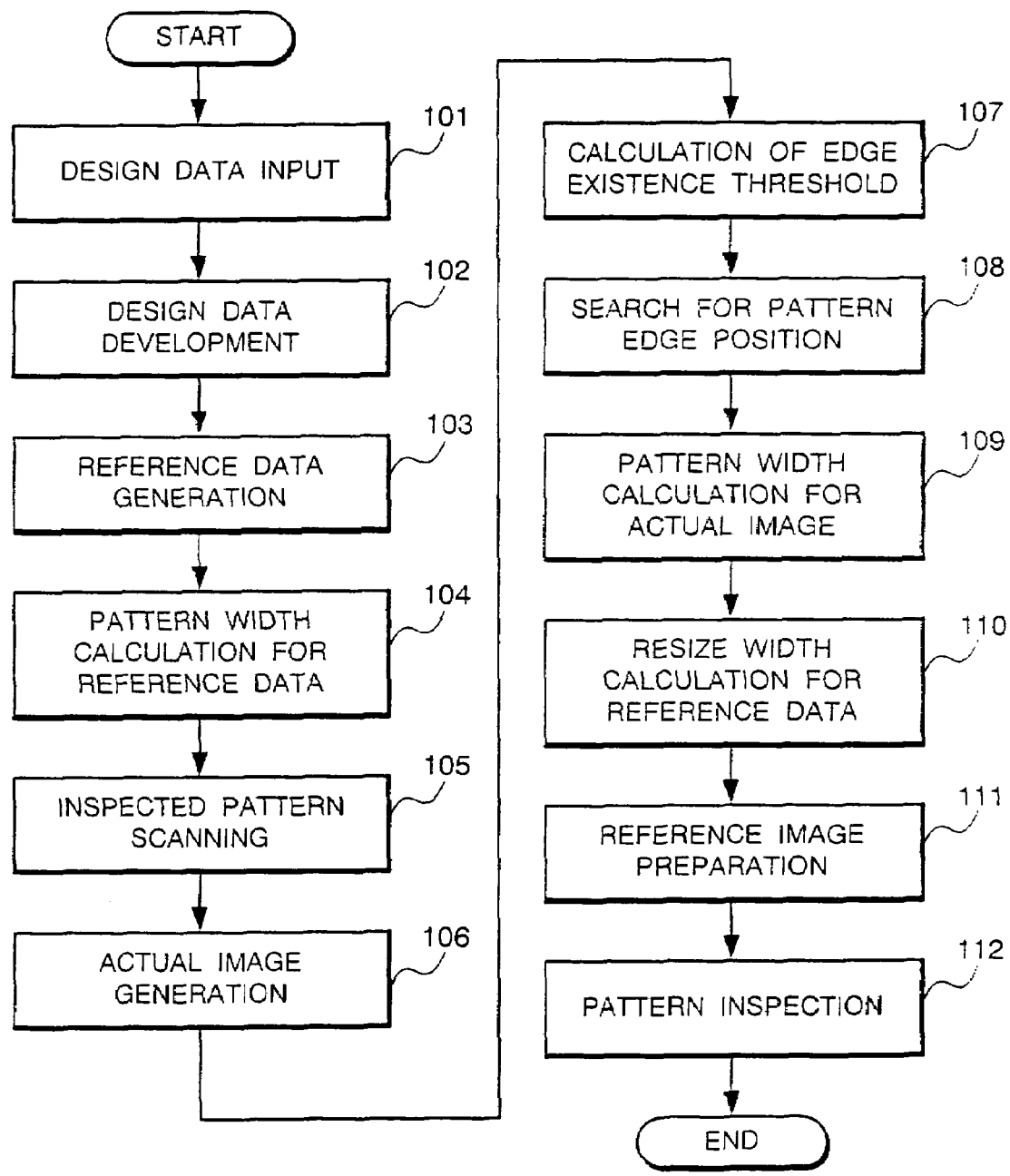
FIG. 2 is a flowchart to illustrate the operation of the pattern inspection device as shown in FIG. 1.

Next, referring to the attached figures, a preferred embodiment of the present invention will be described in details below. FIG. 1 is a block diagram of a pattern inspection device as a first embodiment of the present invention and FIG. 2 is a flowchart showing the operation of the pattern inspection device as shown in FIG. 1.

It is necessary to inspect fine patterns of the semiconductor integrated circuit or the like formed on the photo-mask, reticle and wafer liquid crystal to see whether they are correctly drawn according to the dimensions and shapes of the ideal pattern prepared from the design data by pattern inspection device.

In this type of pattern inspection device, the design data given with square or trapezoid position coordinates and line length are firstly expressed as binary bit string consisting of "0" and "1" corresponding to the inspected pattern. Density values in a pixel are generated by integration of the bit string within the pixel width of a predetermined resolution.

Next, a certain optical point spread function is prepared based on the pattern information obtained by scanning the inspected pattern with the laser beam and making an image on the light receiving device with the light which has passed the pattern or based on the edge profiling of the pattern image obtained from the image sensing system. Using this function and executing the convolution operation with the multiple gray scale data (multi-value data) in the design data, the reference image is obtained.

Defects on the inspected pattern are detected by reading the reference image obtained from the design data synchronizing with the image of the inspected pattern obtained by optical scanning or by input from the image sensing system and by finding discrepancies between the image of the inspected pattern and the reference image at corresponding pixel positions (Die-To-Data BASE inspection).

Under the optical conditions and influence of the manufacturing processes, the image of the inspected pattern has thicker or thinner line widths and other dimensional errors when compared with the ideal design values. Pseudo discrepancies from the reference image obtained from the design data tend to result in pseudo defects, which should not be judged as defects.

Therefore, it is necessary to execute appropriate characteristics extraction such as edge position detection corresponding to the characteristics amount in each inspection zone and to correct in advance the pattern width of the multiple gray scale image in the design data before convolution processing with the optical point spread function so that such width comes to the edge position of the image in the inspected pattern.

A pattern inspection device according to this embodiment comprises an optical scanning section 4 which outputs a scan signal 14 by scanning the wiring pattern to be inspected i.e. the inspected pattern with the laser beam and a photoelectric image processing section 5 which converts the scan signal 14 to output an actual image 15 with multi-valued gray scales.

Further, the pattern inspection device is provided with a design data input section 1 to which design data 11 described in MEBES (Manufacturing Electron Beam Exposure System) defining the figure dimensions of the inspected pattern is input, a design data developing section 2 which develops the design data 11 to a wiring pattern and prepares reference data 12 with multiple gray scales, a reference image generation section 3 which prepares a reference image 13 by correcting the wiring patterns in the reference data 12 to make them closer to the patterns in the actual image 15, an image memory 6 to store the actual image 15 obtained by the photoelectric image processing section 5 and the reference image 13 obtained by the reference image generation section 3, and a data comparison section 7 which inspects the inspected pattern by comparing the actual image 15 of the inspected pattern obtained by optical scanning and the reference image 13 prepared from the design data 11. The reference data 12, the reference image 13 and the actual image 15 are given as data showing the gray scale values in 256 levels for each pixel in a frame having 512 pixels in X (horizontal) direction and 512 pixels in Y (vertical) direction.

The reference image generation section 3 further comprises an edge position detection means to detect the edge position of the actual image 15 (image of the inspected pattern) by the unit of sub-pixels and a pattern width calculation means to calculate the pattern width of the actual image 15 and the pattern width of the reference data 12 at the corresponding position.

Next, referring to the figures, the operation of the present invention is described below. First of all, the data structure of the design data is described.

To the design data input section 1, the design data 11 described in MEBES or other format is input (Step 101 in FIG. 2).

Then, the design data developing section 2 develops the design data 11 input from the design data input section 1 to the pixels arranged on a lattice corresponding to the addresses of the pattern coordinates of the actual image 15 so as to form a wiring pattern 21 (Step 102 in FIG. 2).

Figure 3:
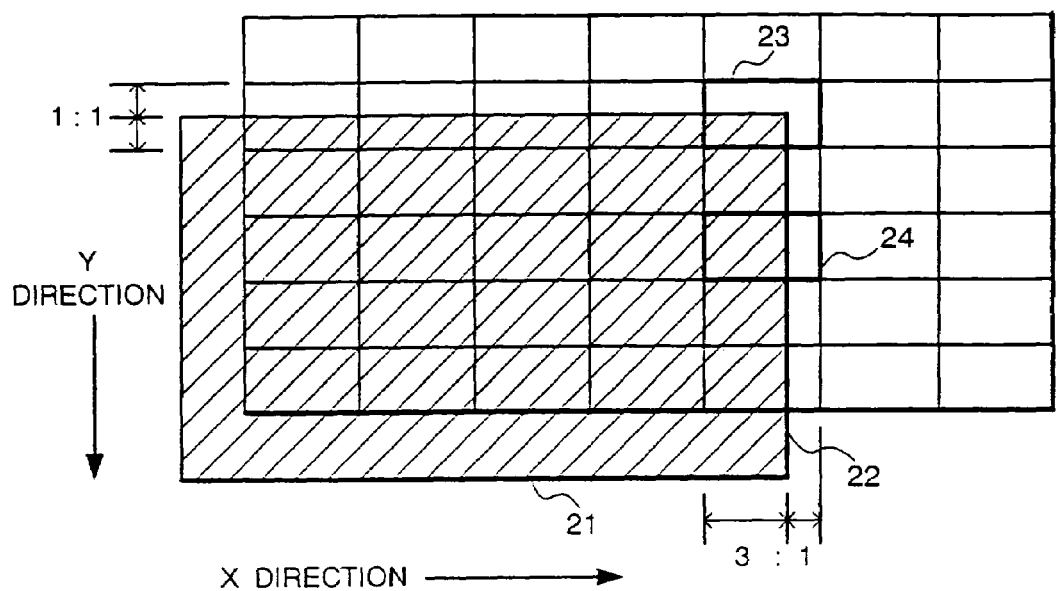
FIG. 3 is an explanatory view showing a part of the wiring pattern developed by the design data developing section.

FIG. 3 is an explanatory view showing a part of the developed wiring pattern 21. In FIG. 3, the pixels arranged on a lattice correspond to the development resolution at the design data developing section 2.

In the example of FIG. 3, an edge 22 of the wiring pattern 21 is not at a break of the pixels. On a pixel 23, for example, the edge is developed to be at the position of 3:1 ratio in X (horizontal) direction and 1:1 ration in Y (vertical) direction.

Each pixel has several sub-pixels to calculate the gray level value (density) of multi-valued gray scales at a finer resolution than the inspection resolution. The accuracy of the gray level values for each pixel depends on the number of such sub-pixels.

For example, when the data is developed for the maximum gray level of 255 and the minimum gray level of 0, and the gray level increment (hereinafter referred to as the gray level step count) of 1, one pixel consists of 16×16 sub-pixels. Each sub-pixel has either 0 or 1.

Figure 4:
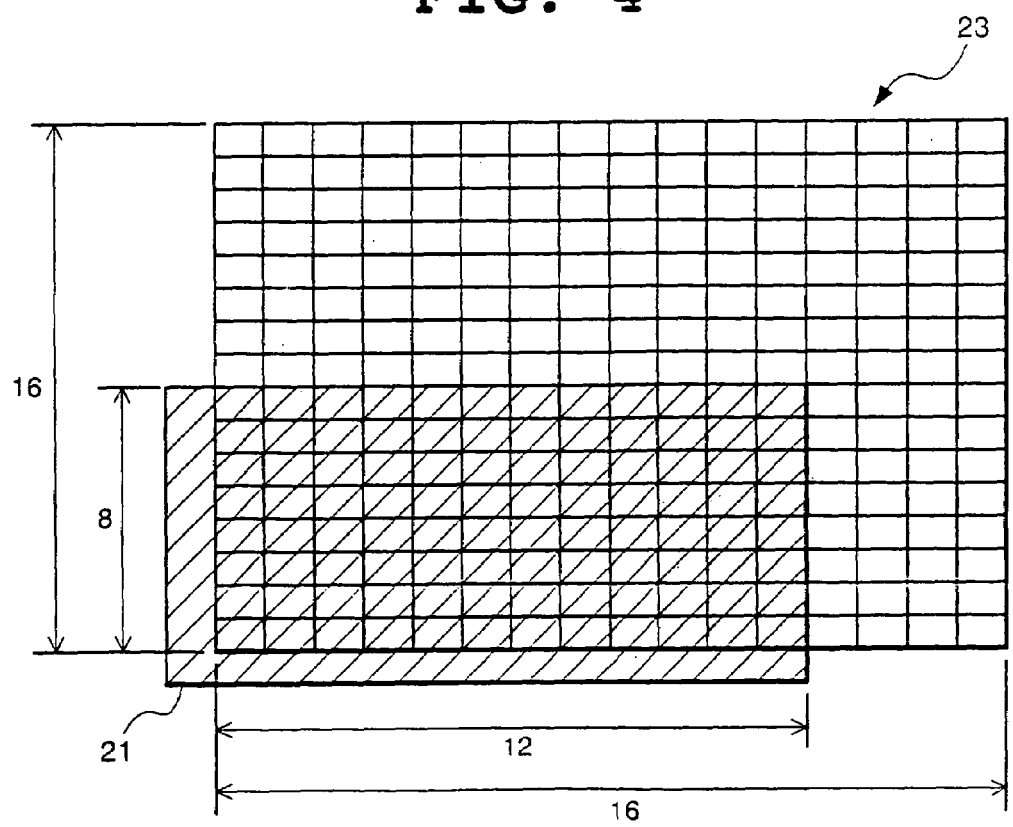
FIG. 4 is an enlarged view of a pixel in FIG. 3.

FIG. 4 is an enlarged view of the pixel 23 shown in FIG. 3. In the example of FIG. 4, the wiring pattern 21 is on the 8×12 sub-pixels among 16×16 sub-pixels in the pixel 23.

Suppose here that the sub-pixels belonging to the wiring pattern 21 are shown with "1" and the sub-pixels not belonging to the wiring pattern 21 are shown with "0". The gray level value of each pixel is the number of sub-pixels belonging to the pattern 21 in that pixel, or the number of "1".

Therefore, the gray level value of the pixel not belonging to the wiring pattern 21 is the minimum gray level value MIN=0 and the pixels at positions other than the pattern edge among the pixels belonging to the wiring pattern 21 have the maximum gray level value MAX=255. The pixels at the pattern edge position partially belonging to the wiring pattern 21 have, in case of the pixel 23, for example, 8×12=96 as the gray level value.

Figures 5, 6:
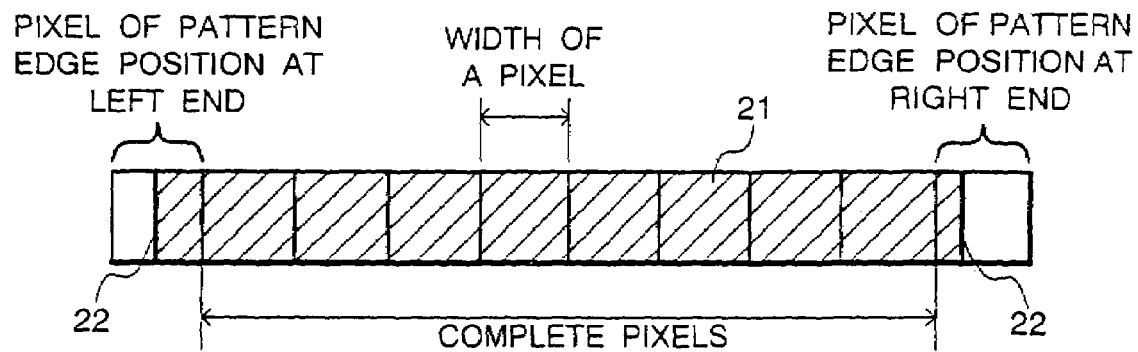
FIG. 5 is an explanatory view to show the gray level values of the pixels in the wiring pattern of FIG. 3.
FIG. 6 is an explanatory view to illustrate the method to calculate the pattern width in the reference data.

Thus, as shown in FIG. 5, the gray level value of the developed wiring pattern 21 can be calculated for each pixel i.e. each address of the pattern coordinates for the actual image 15 by integrating the areas of the bit string in the pixel.

After developing the wiring pattern 21 on the pixels based on the design data 11 (Step 102 in FIG. 2), the design data developing section 2 executes bit integration for each pixel and calculates the gray level value, which is a multiple of the gray level step count as described above and outputs the result as the reference data 12 corresponding to the actual image 15 (Step 103 in FIG. 2). Though the design data 11 is developed by the design data developing section 2 in this embodiment, the design data 11 is not necessarily input directly to the design data input section 1. The design data 11 may be converted to an intermediate file suitable for memory development in advance so that such intermediate file is input for the design data 11 and the intermediate file is developed by the design data development section 2.

Next, the method to calculate the pattern width of the reference data 12 is explained below. The pattern width of the reference data 12 is calculated by the reference image generation section 3 (Step 104 in FIG. 2).

First of all, the pixel width $N_{step}$ of the reference data 12 is defined as follows based on the structure of the design data 11:

Pixel width $N_{step}$=Maximum gray level MAX of white pixel/Gray level step count  (1)

According to the definition of formula (1), it is necessary that the pixel width $N_{step}$ is a positive multiple of the gray level step count and the gray level step count is a common divisor of the maximum gray level MAX.

Supposing that the gray level step count is 1, the pixels at positions other than the pattern edge among the pixels belonging to the wiring pattern 21 have the maximum gray level MAX=255 as described above. Thus, the horizontal width of the pattern 21 existing in this pixel is the pixel width $N_{step}$ and, when the gray level step count is 1, is equal to the gray level value 255.

In FIG. 3, the gray level value of a pixel 24 having the pattern edge 22 of the wiring pattern 21 inside is 12×16=192. Therefore, the distance from the pattern edge 22 to the left edge of the pixel 24 is, according to the definition of formula (1) and supposing the gray level step count to be 1, (12×16)/1=192.

The definition of formula (1) can be applied not only to the horizontal direction but also to the vertical direction similarly. When the gray level step count is 1, the distance is always equal to the gray level value and calculation errors occur the least.

For example, the pattern width of the reference data (wiring pattern 21) as shown in FIG. 6 is the distance between the pattern edges on the right and the left. It can be defined as follows:

Pattern width of reference data={(Gray level value of the pixel at left end pattern edge position/ Gray level step count)+(Gray level value of the pixel at right end pattern edge position/Gray level step count)+Number of complete pixels between right and left pattern edges×$N_{step}$}  (2)

In formula (2), "complete pixels" represent the pixels belonging to the pattern 21 excluding the pixels at the pattern edge position.

Thus, by providing each pixel with sub-pixels forming a matrix in the pixel, calculating the gray level value of the pixels based on the number of sub-pixels belonging to the pattern developed in the pixels, considering the count obtained by division of the gray level value by the gray level step count to be the width of the pattern developed in the pixel and totaling the width of the pattern developed in the pixels, the pattern width of the reference data 12 can be determined.

Next, the optical scanning section 4 scans the inspected pattern formed on the substrate with optical transmission property such as photo-mask using the laser beam of the predetermined wavelength and makes an image of the transmission light which has passed through the above substrate on the light receiving device using an objective lens and outputs the image of the inspected pattern obtained by this light receiving device as the scanning signal 14 (Step 105 in FIG. 2).

Then, as described later, the photoelectric image processing section 5 executes the convolution operation of the inspected pattern image output as the scanning signal 14 and the optical point spread function and obtains the actual image 15 with multi-valued gray levels (Step 106 in FIG. 2). This actual image 15 is stored to the image memory 6.

Next, the method to calculate the pattern width of the actual image 15 stored in the image memory 6 is explained below. In the actual image 15, the gray level value and the pixel width are defined in the same way as in the reference data 12. The pattern width of the actual image 15 can be determined by calculation of the edge existence threshold (Edge boundary condition), search for the pattern edge position and pattern width calculation, which are executed by the reference image generation section 3 in FIG. 1.

In the image processing, the edge position is generally detected with extracting the edge position by the unit of pixels as a set of maximum values of the gray level gradient between the operator mask center and the adjacent pixel as in Sobel filtering or a set of pixel addresses where zero crossing or other secondary differentiation value is 0. However, the edge of the digital observation image is not always positioned at a break of pixels. Particularly, when testing micro patterns for 256 M and 1 G DRAM masks, which are subjects of the inspection by the reticle inspection device, it is necessary to detect the pattern edge position with an accuracy of 1 pixel or less. By conventional edge position detection methods by the unit of pixels, the accuracy of the pattern width determination is limited.

In the present invention, the pattern edge position is detected from the light amount fluctuation in the mask operator, which corresponds to beam scanning. When the laser beam diameter required for pattern edge extraction is sufficiently small and shading error (Error in light amount fluctuation) in the scanned image is small, the pattern edge position can be determined to the sub-pixel accuracy.

Figure 7:
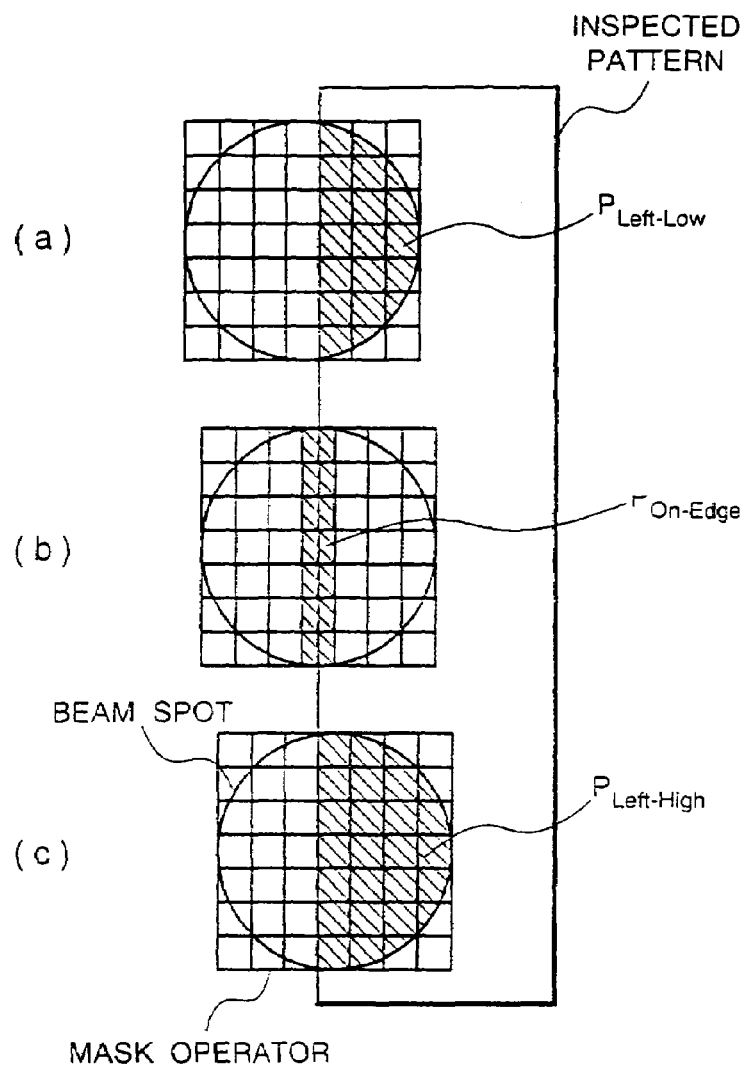
FIG. 7 is an explanatory view to illustrate the method to calculate the threshold for edge existence.

FIG. 7 is an explanatory view showing the method to calculate the edge existence threshold. FIG. 7(a) shows the status immediately before the mask operator center comes to the inspected pattern formed on the photo mask or other substrate, FIG. 7(b) shows the status when the mask operator center is on the edge position of the inspected pattern and FIG. 7(c) shows the status when the mask operator center is at the limit of the edge position of the inspected pattern. The mask operator consisting of a unit lattice of 7×7 shows the beam scanning position and at the same time shows the position for convolution operation of the optical point spread function and the inspected pattern image.

Formulation of the actual image 15 stored in the image memory 6 is explained here. The gray level value of the actual image 15 is expressed as the convolution function obtained from the optical point spread function $\omega_{[k][j]}$ for the machine system and the inspected pattern image $I_{[x][y]}$ formed on the photo-mask or other substrate. In case of FIG. 7(c), the gray level value L (X, Y) of the actual image 15 at the position of the address in the frame (X, Y) is expressed as follows.

$$L(X, Y) = \left( \sum_{-3 \leq k \leq 3} \sum_{-3 \leq j \leq 3} \omega_{[k][j]} \right) \times I_{[X+k][Y+j]} \quad (3)$$

The optical point spread function $\omega_{[k][j]}$ (where $-3 \leq k \leq 3$ and $-3 \leq j \leq 3$) represents the coefficient of the convolution filter, which shows blur of the image, and represents, from the optical viewpoint, the laser beam strength (transmission light amount) in the mask operator for every unit lattice of the mask operator.

When etching is in a good condition, the inspected pattern formed on the photo-mask or other substrate can be considered to be a multi-value image extremely close to a binary image. Thus, to facilitate the explanation, it is supposed here that the inspected pattern with infinite length on the substrate is at a break of the pixels and the laser beam position is as shown in FIG. 7(c). When the gray level value of the black pixel of the actual image 15 (pixel not belonging to the inspected pattern) is d_min and the gray level value of the white pixel (pixel belonging to the inspected pattern is d_max, formula (3) can be converted to the formula below.

$$L(X, Y) = \begin{bmatrix} \omega_{[-3][-3]} & \omega_{[-2][-3]} & \omega_{[-1][-3]} \\ \omega_{[-3][-2]} & \omega_{[-2][-2]} & \omega_{[-1][-2]} \\ \vdots & \vdots & \vdots \\ \omega_{[-3][-2]} & \omega_{[-2][-2]} & \omega_{[-1][2]} \\ \omega_{[3][3]} & \omega_{[2][3]} & \omega_{[-1][3]} \end{bmatrix} \times d\_min +$$

$$\begin{bmatrix} \omega_{[0][-3]} & \omega_{[1][-3]} & \omega_{[2][-3]} & \omega_{[3][-3]} \\ \omega_{[0][-2]} & \omega_{[1][-2]} & \omega_{[2][-2]} & \omega_{[3][-3]} \\ \vdots & \vdots & \vdots & \vdots \\ \omega_{[0][2]} & \omega_{[1][-2]} & \omega_{[2][2]} & \omega_{[2][3]} \\ \omega_{[0][3]} & \omega_{[1][3]} & \omega_{[2][3]} & \omega_{[3][3]} \end{bmatrix} \times d\_max$$

$$= \left( \sum_{\substack{-3 \le k \le -1 \\ -3 \le j \le 3}} \omega_{[k][j]} \right) \times d\_min +$$

$$\left( \sum_{\substack{0 \le k \le -1 \\ -3 \le j \le 3}} \omega_{[k][j]} \right) \times d\_max$$

(4)

The first term on the right side of formula (4) represents the gray level value of the black pixel zone and the second term on the right side represents the gray level value of the white pixel zone.

Total light amount, which is obtained by totaling all of the optical point spread functions $\omega_{[k][j]}$ on 7×7 lattice, is normalized to 1 and the sum of the optical point spread functions belonging to the white pixel zone $\omega_{[k][j]}$ and the optical point spread functions belonging to the black pixel zone $\omega_{[k][j]}$ is expressed as follows:

$$\sum_{\omega \in white} \omega_{[k][j]} + \sum_{\omega \in black} \omega_{[k][j]} = \sum_{\omega \in all} \omega_{[k][j]} = 1 \quad (5)$$

In formula (5), $\omega \in$ white shows that the term immediately above is the sum of the optical point spread functions $\omega_{[k][j]}$ belonging to the white pixel zone and $\omega \in$ black shows that the term immediately above is the sum of optical point spread functions $\omega_{[k][j]}$ belonging to the black pixel zone, and $\omega \in$ all shows that the term immediately above represents the total light amount. From formula (5), the formula below can be obtained.

$$\sum_{\omega \in black} \omega_{[k][j]} = 1 - \sum_{\omega \in white} \omega_{[k][j]} \quad (6)$$

In the reality, the laser beam spot has an asymmetrical shape. When it is converted to a circle, however, the optical point spread function $\omega_{[k][j]}$ for each unit lattice can be converted to the light amount value $W_{[k][j]}$. From the light amount value $W_{[k][j]}$ and formulas 5 and 6, the following formula can be obtained.

$$L(X,) = d\_min + \frac{\sum_{W \in white} W_{[k][j]}}{\sum_{W \in all} W_{[k][j]}} \times (d\_max - d\_min) \quad (7)$$

In formula (7), W ∈ white shows that the term immediately above represents the sum of the light amount value $W_{[k][j]}$ belonging to the white pixel zone, and W ∈ all shows that the term immediately above represents the total light amount, which is the sum totaling all of the light amount values $W_{[k][j]}$ in 7×7 lattice. Formula (7) means that the ratio of the light amount for the white pixel zone in the total light amount, which changes as the beam moves, controls the inclination of the edge profile.

Figure 8:
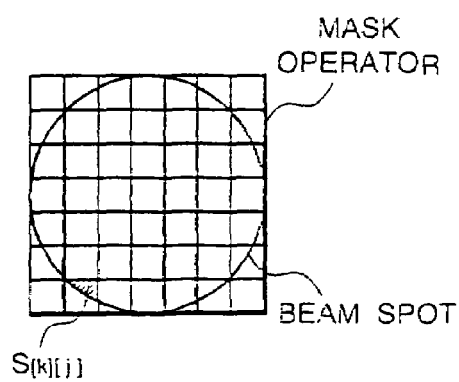
FIG. 8 is an explanatory view to illustrate the occupied area in a unit grid of the laser beam spot.

The elements of the 7×7 light amount table are area ratios of the beam shape in each unit lattice when the lattice is divided (FIG. 8) and the relation between the light amount $W_{[k][j]}$ in each unit lattice and the area of the laser beam spot in the unit lattice (hereinafter referred to as the unit lattice occupation area) $S_{[k][j]}$ is as follows:

$$W_{[k][j]} = 255 \times S_{[k][j]} \quad (8)$$

The unit lattice occupation area $S_{[k][j]}$ of the laser beam is the value when the beam spot is converted to a circle. From the unit lattice occupation area $S_{[k][j]}$, the optical point spread function $\omega_{[k][j]}$ can be expressed as follows:

$$\omega_{[k][j]} = \frac{\sum_{W \in white} W_{[k][j]}}{\sum_{W \in all} W_{[k][j]}} = \frac{255 \times \sum_{S \in white} S_{[k][j]}}{255 \times \sum_{S \in all} S_{[k][j]}} \quad (9)$$

In formula 9, S ∈ white represents that the term immediately above shows the sum of the unit lattice occupation area $S_{[k][j]}$ belonging to the white pixel zone and S E all represents that the term immediately above shows the total beam spot area, which is the sum totaling all of the unit lattice occupation areas $S_{[k][j]}$. From the formulas (7) and (9), the gray level value L (X, Y) of the actual image 15 can be expressed as follows:

$$L(X, Y) = d\_min + \frac{\sum_{S \in white} S_{[k][j]}}{\sum_{S \in all} S_{[k][j]}} \times (d\_max \times d\_min) \quad (10)$$

Formula (10) shows that the gray level at the laser beam position can be easily determined from the area occupied by the beam spot and the area of the zone where the beam spot is over the inspected pattern on the photo-mask. This means that, even when the laser beam is asymmetrical or of any shape, the gray level on the edge profile can be determined without depending on local changes in density of the inspected pattern on the photo mask, only if the laser beam strength, gray level for black pixels and gray level for white pixels are given in advance.

When the influence of diffraction can be ignored, the pattern edge position on the photo mask or other substrate is the point where the transmitted light amount is reduced by 50%. The position where the ratio between the sum of the light amount (beam spot area) for the section where the laser beam is over the light shading zone (inspected pattern) and the total light amount (whole beam spot area) is ½ is defined to be the pattern edge position (FIG. 7(b)).

Values on the 7×7 light amount table are always converted to the unit lattice occupation area ratio for a circle with a radius R. Thus, the beam occupation area over the pattern at an arbitrary position within the lattice section corresponding to the width of a pixel can be determined by analysis. Therefore, by setting an appropriate coordinate system and taking an integration section value below the pixel resolution, the edge position by the unit of sub-pixels can be easily determined.

Next, the reference image generation section 3 calculates the edge existence threshold, which is the gray level corresponding to the pattern edge position (Step 107 in FIG. 2). The observed image is subjected to gray level modulation due to electronic beam drawing and chemical processes and further affected by changes of the shape and gray level in the optical system and detection system. The actual image 15 defined here shall be the processed image after convolution operation using 7×7 optical point spread function and the inspected pattern image (512×512 pixels).

The edge existence threshold is determined as follows. Suppose first that the total light amount immediately before the mask operator center comes to the inspected pattern formed on the photo-mask or other substrate as in FIG. 7(a) is $W_{Left-Low}$, the total light amount when the mask operator center is on the edge position of the inspected pattern as shown in FIG. 7(b) is $W_{On-Edge}$ and the total light amount when the mask operator center is at the limit of the edge position of the inspected pattern as shown in FIG. 7(c) is $W_{Left-High}$.

When the laser beam spot diameter is sufficiently small, the increase/decrease ratio of the light strength distribution in the width of a pixel is linear in relation to the position in the pixel, and the convolution operation value $P_{Left-Low}$, which is the gray level of the mask operator center in the status of FIG. 7(a) can be determined by the formula below based on formula (9):

$$P_{Left-Low} = d\_\min + \frac{W_{Left-Low}}{W_{all}}(d\_\max \times d\_\min) \quad (11)$$

In formula 11, $W_{all}$ represents the total light amount when no inspected pattern is over the beam spot and the transmission light ratio is 100%.

Similarly, in the status of FIG. 7(b) where the mask operator center is on the pattern edge position, the convolution operation value $P_{On-Edge}$, which is the gray level of the mask operator center, can be determined by the formula below.

$$P_{On-Edge} = d\_\min + \frac{W_{On-Edge}}{W_{all}}(d\_\max - d\_\min) \quad (12)$$

Note that, however, the pattern edge is at the position where the transmission light ratio is 50% and the relation of the formula below exists.

$$W_{On-Edge} = W_{all}/2 \quad (13)$$

In the status of FIG. 7(c) where the pattern edge exists and the beam spot and the inspected pattern are overlapped for the largest area, the convolution operation value $P_{Left-High}$ can be calculated from the formula below.

$$P_{Left-High} = d\_\min + \frac{W_{Left-High}}{W_{all}}(d\_\max - d\_\min) \quad (14)$$

Therefore, the condition for the pattern edge to be at sub-pixel positions below the width of a pixel is as represented by the formula below and is stored in the memory of the reference image generation section 3 as the edge existence threshold value. This completes the calculation of the edge existence thresholds $P_{Left-Low}$, $P_{On-Edge}$ and $P_{Left-High}$.

$$P_{Left-Low} < P_{On-Edge} < P_{Left-High} \quad (15)$$

Figure 9:
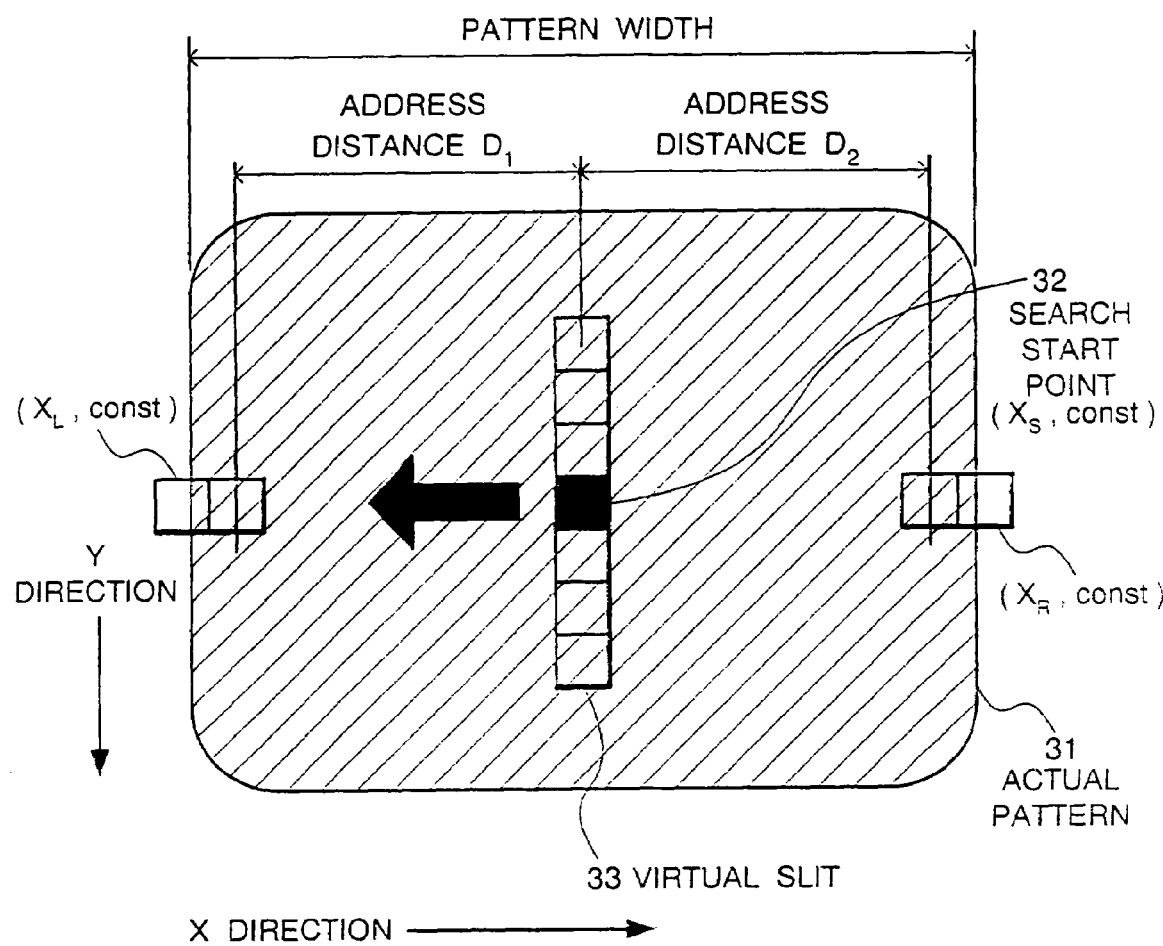
FIG. 9 is an explanatory view to illustrate the method to search for the pattern edge in each unit of pixel for the actual image.
Figure 10:
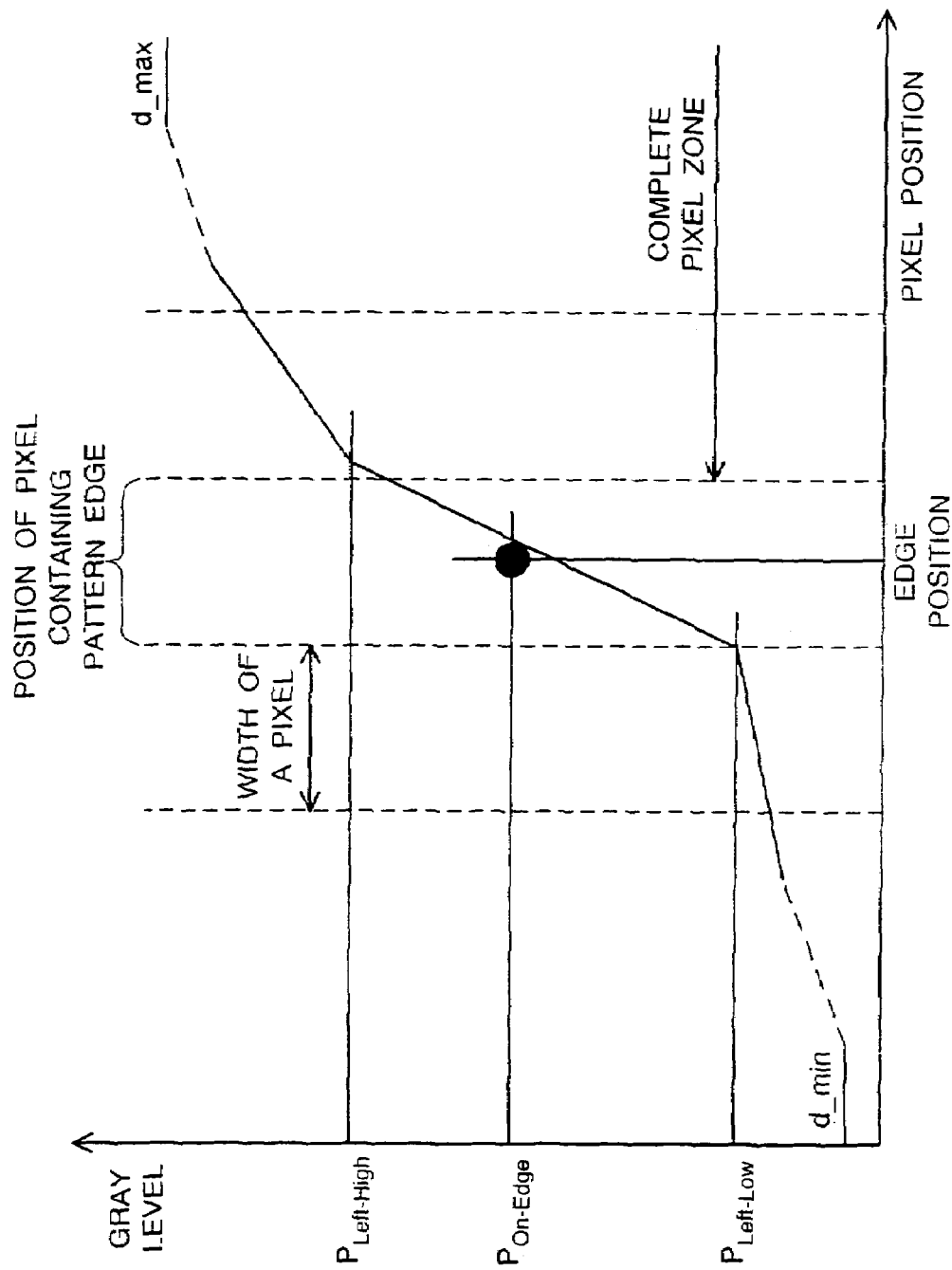
FIG. 10 is an explanatory view to illustrate the method to search for the pattern edge in each unit of sub-pixel for the actual image.

Next, the reference image generation section 3 searches for the right and left pattern edge positions based on these edge existence thresholds $P_{Left-Low}$, $P_{On-Edge}$ and $P_{Left-High}$ (Step 108 in FIG. 2). Firstly, the pattern edge search for the left is explained. FIG. 9 and FIG. 10 are explanatory views illustrating the method to search for the pattern edge in the actual image 15. FIG. 9 shows an example of an actual pattern 31 stored in the image memory 6 as the actual image 15. FIG. 10 shows the edge profile near the left pattern edge of the actual pattern 31.

Suppose, in FIG. 9, that the coordinates of an arbitrary position on the actual image 15 for 1 frame to be (X, Y) and the gray level of the actual pattern 31 at that position to be L(X, Y). In this embodiment, the pattern edge search for the left is executed by the unit of pixels first.

The pattern edge search by the pixel unit is conducted with moving to the left in parallel with the X axis starting from a search start point 32 in the white pixel zone on the actual pattern 31 corresponding to the start position for pattern width measurement in the design data. The coordinates of the search start point 32 are supposed to be ($X_S$, const).

The actual image 15 has gray level variations because of shot noise, influence from the image sensing system and pattern edge manufacturing conditions.

To exclude the influence caused by such gray level variations, a virtual slit 33 having a certain width is supposed in the direction perpendicular to the search direction around the search point (Initial value of X coordinate is $X_S$ and Y coordinate is const). The range of the virtual slit 33 is treated as the pattern edge search range for the search point coordinates (X, const).

The virtual slit 33 may have any width, but it has a width corresponding to 7 pixels in the example shown in FIG. 9.

The gray level L (X, const) for the search point coordinates (X, const) is the average of the gray levels at the pixels remaining after the pixel with the highest gray level and the pixel with the lowest gray level are excluded from several pixels constituting the virtual slit 33.

In other words, in the case of FIG. 9, the gray level L (X, const) at the search point coordinates (X, const) is determined as follows:

$$L(X, const) = \left\{ \sum_{-3<i<3} L(X, const+i) \right\} / 5 \quad (16)$$

For the pixels where the left pattern edge is positioned, the following formula applies.

$$P_{Left-Low} < L(X, const) < P_{Left-High} \qquad (17)$$

In the complete pixel as described above, L (X, const) $\geq P_{Left-High}$.

Therefore, the reference image generation section 3 repeats, with moving the virtual slit 33 to the left by the unit of pixels, determination of the gray level L (X, const) and judgement whether the pixel at the search point is a complete pixel or not for each pixel unit. Then, the reference image generation section 3 counts the number of feeds from the search start point 32, or the number of complete pixels to the point immediately before the left pattern edge position.

When the laser beam spot diameter is sufficiently small and the etching of the inspected pattern formed on the photo-mask is in a good condition, the pattern edge position is contained in the range of ±one pixel. Therefore, when L(X, const)<$P_{Left-High}$ is established for the first time, it can be judged that the search point at the center of the virtual slit 33 comes to the position of the pixel containing the left pattern edge.

Considering the coordinates of the pixel containing the left pattern edge to be ($X_L$, const) here, the address distance $D_1$ between this pixel and the pixel of the search start point 32 always coincides the complete pixel zone.

Since the X coordinate $X_L$ of the pixel containing the left pattern edge shown in FIG. 9 can be determined by $X_S - D_L$, the pattern length $N_{L-Complete}$ of the complete pixel zone from the search start point 32 to the point immediately before the left pattern edge position can be obtained by the formula below.

$$N_{L-Complete} = (Xs - D1) \times N_{step} \qquad (18)$$

Next, the reference image generation section 3 makes the pattern edge search by the unit of sub-pixels. When the resolution is sufficiently small, the light amount integration within a pixel transits linearly as shown in FIG. 10 and the distance $N_{Left-Sub}$ in the unit of sub-pixels from the boundary between the pixel containing the left pattern edge and the complete pixel adjacent to such pixel to the left pattern edge can be described as follows:

$$N_{Left-Sub} = \begin{cases} N_{step} - \dfrac{P_{Left-High} - P_{Left-Low}}{P_{On-Edge} - P_{Left-Low}} \times N_{step} & (19) \\ (\text{when } P_{Left-Low} < L(X, const) < P_{Left-High}) \\ 0 \\ (\text{when } L(X, const) - P_{Left-Low}) < 0) \end{cases}$$

Therefore, the distance $LENGTH_{S-L}$ from the search start point 32 to the left pattern edge can be calculated as follows based on formulas (18) and (19).

$$LENGTH_{S-L} = N_{Left-Sub} + N_{L-Complete} \qquad (20)$$

Then, the reference image generation section 3 searches for the right pattern edge toward the right side by the unit of pixels starting from the search start point 32 using the virtual slit 33 similarly to the search for the left as described above. Here, the formula below applies to the pixels where the right pattern edge is positioned.

$$P_{Right-Low} < L(X, const) < P_{Right-High} \qquad (21)$$

In formula (21), $P_{Right-Low}$ is the convolution operation value serving as the gray level value of the mask operator center when the mask operator center is at the position immediately before the inspected pattern and $P_{Right-High}$ is the convolution operation value when the mask operator center is at the limit of the pattern edge position. The relation between the mask operator center and the inspected pattern is as shown in FIG. 7 with its right and left reversed.

In the complete pixel, L(X, const)$\geq P_{Right-High}$. Therefore, the reference image generation section 3 repeats, with moving the virtual slit 33 to the right by the unit of pixels, determination of the gray level L (X, const) and judgement whether the pixel at the search point is a complete pixel or not for each pixel unit. Then, the reference image generation section 3 counts the number of complete pixels to the point immediately before the right pattern edge position.

When L(X, const)<$P_{Right-High}$ is established for the first time, the reference image generation section 3 judges that the search point at the center of the virtual slit 33 comes to the position of the pixel containing the right pattern edge.

Considering the coordinates of the pixel containing the right pattern edge to be ($X_R$, const), the address distance $D_2$ between this pixel and the pixel of the search start point 32 always coincides the complete pixel zone.

Since the X coordinate $X_R$ of the pixel containing the right pattern edge shown in FIG. 9 can be determined by $X_s - D_2$, the pattern length $N_{R-Complete}$ of the complete pixel zone from the search start point 32 to the point immediately before the right pattern edge position can be obtained by the formula below.

$$N_{R-Complete} = (Xs + D2) \times N_{step} \qquad (22)$$

Next, the reference image generation section 3 makes the pattern edge search by the unit of sub-pixels similarly to the search for the left as described above. The distance $N_{Right-sub}$ in the unit of sub-pixels from the boundary between the pixel containing the right pattern edge and the complete pixel adjacent to such pixel to the right pattern edge can be described as follows:

$$N_{Right-Sub} = \begin{cases} \dfrac{P_{Right-High} - P_{Right-Low}}{P_{On-Edge} - P_{Right-Low}} \times N_{step} & (23) \\ (\text{when } L(X_R, const) < P_{Right-Low}) \\ 0 \\ (\text{when } P_{Right-Low} < L(X_R, const) < P_{Right-High}) \end{cases}$$

Therefore, the distance LENGTHS-R from the search start point 32 to the right pattern edge can be calculated as follows based on formulas (22) and (23).

$$LENGTH_{S-R} = N_{Right-Sub} + N_{R-Complete} \qquad (24)$$

From calculations above, the actual pattern width $L_{L-R}$ as the distance between the right and left pattern edges can be obtained as follows with adding the length of the search start point.

$$L_{L-R} = (N_{Left-Sub} + N_{L-Complete}) + (N_{Right-Sub} + N_{R-Complete}) + 1 \qquad (25)$$

Thus, the pattern width of the actual image 15 can be calculated (Step 109 in FIG. 2).

Next, the reference image generation section 3 calculates the resize width (Pattern correction width) Δd for the reference data 12 (Δd may be a positive or negative value) (Step 110 in FIG. 2).

The pattern width may be corrected evenly for each of the left pattern edge and the right pattern edge in the reference data 12. The resize width Δd for the reference data 12 can be calculated as follows based on formula 25.

$$\Delta d = (\text{Actual image pattern width} - \text{Reference data pattern width})/2 \quad (26)$$

Formula (26) shows the resize width for each of the sub-pixels, which are obtained by dividing the width of a pixel $N_{step}$ by 255, when the gray level step count is 1. The formula also shows that the resize width for the reference data 12 is given with the resolution based on the count for the width of 1 pixel when the gray level step count is a common divisor of 255.

Thus, the reference image generation section 3 determines the resize width $\Delta d$ of the pattern width for pixel and sub-pixel units. After moving and correcting the edge position of the wiring pattern in the reference data 12 input from the design data development section 2 according to the resize width $\Delta d$ by the unit of sub-pixels, the reference image generation section 3 executes the convolution operation using the reference data 12 after such pattern width correction and the optical point spread function so as to prepare the reference image 13 close to the actual image 15 (Step 111 in FIG. 2) The reference image 13 is stored in the image memory 6.

The data comparison section 7 compares the reference image 13 stored in the image memory 6 and the actual image 15 and inspects whether the inspected pattern is correctly drawn according to the dimensions and shape of the ideal pattern prepared from the design data (Step 112 in FIG. 2).

Figure 11:
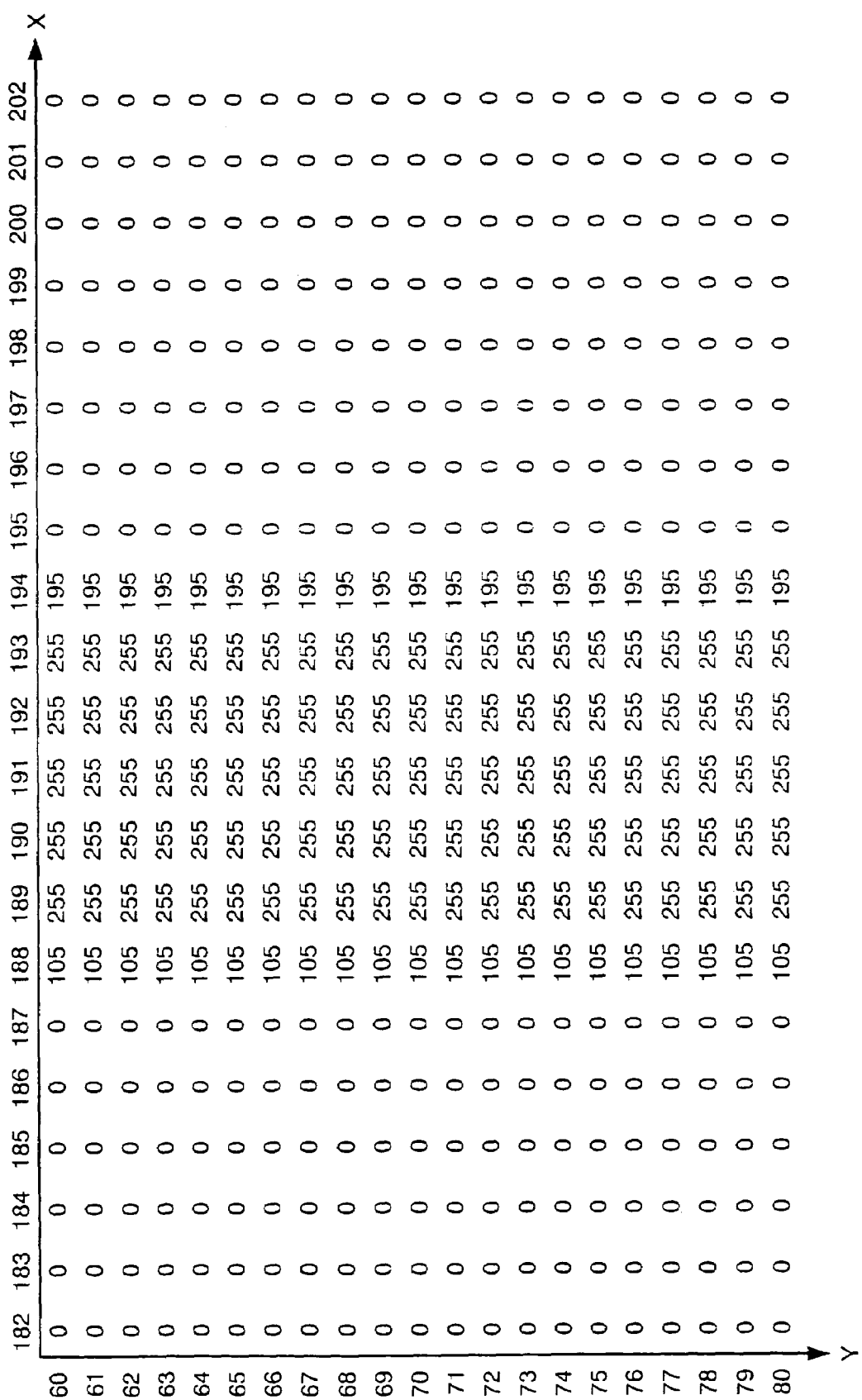
FIG. 11 is an explanatory view to show the gray level distribution of the reference data immediately after development by the design data developing section.

Next, a specific inspection pattern will be explained. FIG. 11 is an explanatory view showing the gray level distribution of the reference data 12 immediately after development by the design data developing section 2. FIG. 11 shows the gray levels for each of the pixels in the zone where X coordinate is 182 to 202 and Y coordinate is 60 to 80. This is an example where the development is made with a proper resolution.

The wiring pattern as shown in FIG. 11 is in the zone where the X coordinate is 188 to 194 and the pattern edge is not at a break of pixels but within a pixel. Supposing that the gray level step count is 1, the pattern width of the reference data 12 shown in FIG. 11 is 1587 from formula (2).

FIG. 12 is an explanatory view illustrating the gray level distribution of the actual pattern at a position corresponding to the reference data 12 of FIG. 11 in the actual image 15. The actual pattern shown in FIG. 12 is in the zone where the X coordinate is 175 to 183. The pattern width of the actual pattern as shown in FIG. 12 is 1757 according to formula (25).

Therefore, the resize width $\Delta d$ to make the edge position of the reference data 12 coincide with the edge position of the actual pattern is, according to formula (26), (1757−1587)/2=78.5. The final resize width $\Delta d$ is the maximum integer not exceeding this value. Thus, the enlarging width of the reference data 12 is 78.

Figure 13:
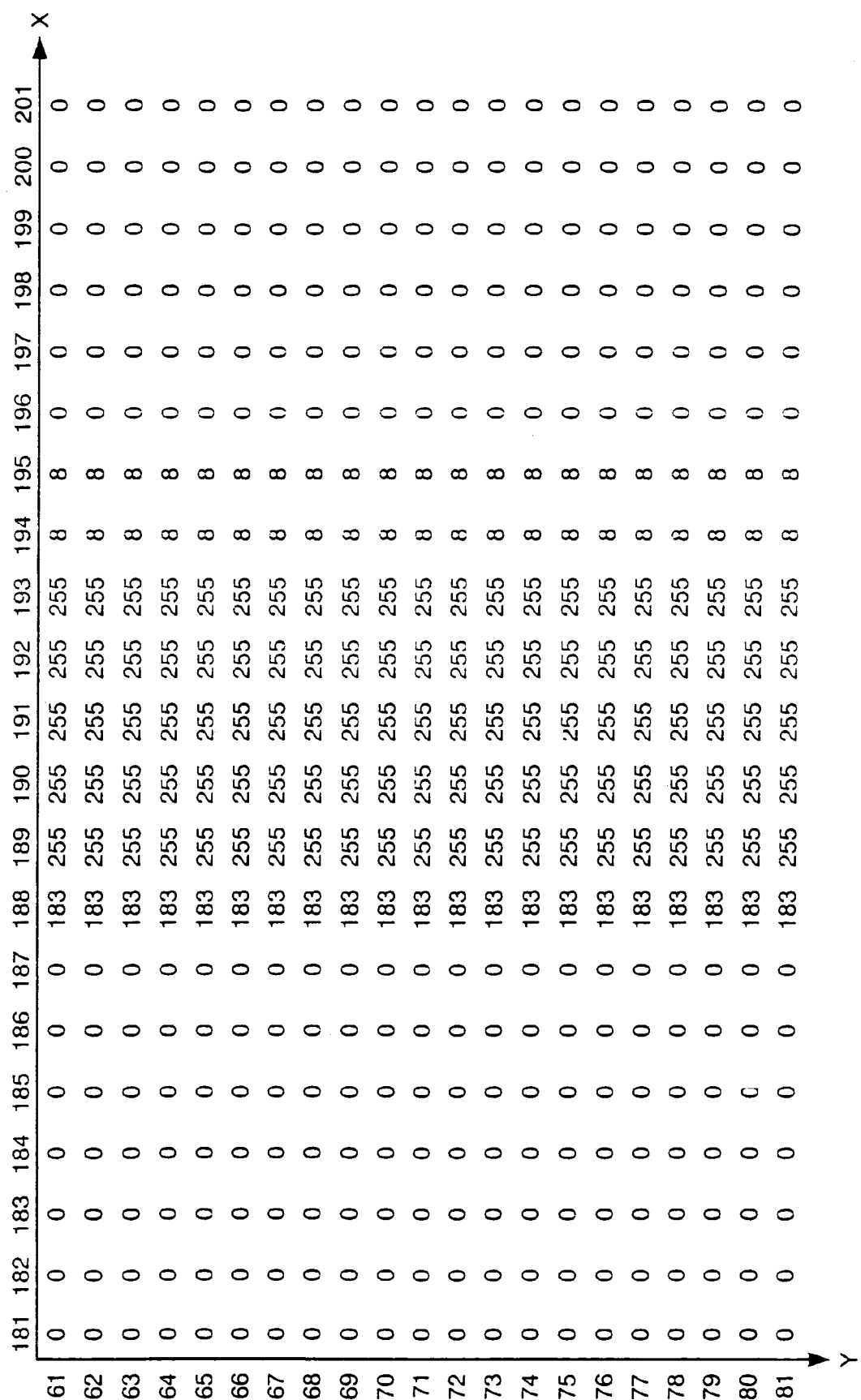
FIG. 13 is an explanatory view to show the result of edge position correction for the reference data in FIG. 11.

FIG. 13 is an explanatory view illustrating the correction result of the edge position in the reference data 12 as shown in FIG. 11. FIG. 14 is an explanatory view showing the 7×7 optical point spread function and FIG. 15 is an explanatory view showing the gray level distribution of the reference image 13 after executing the convolution operation with the optical point spread function of FIG. 14 and the resized reference data 12 of FIG. 13 and aligning the position with the actual image 15.

Figure 15:
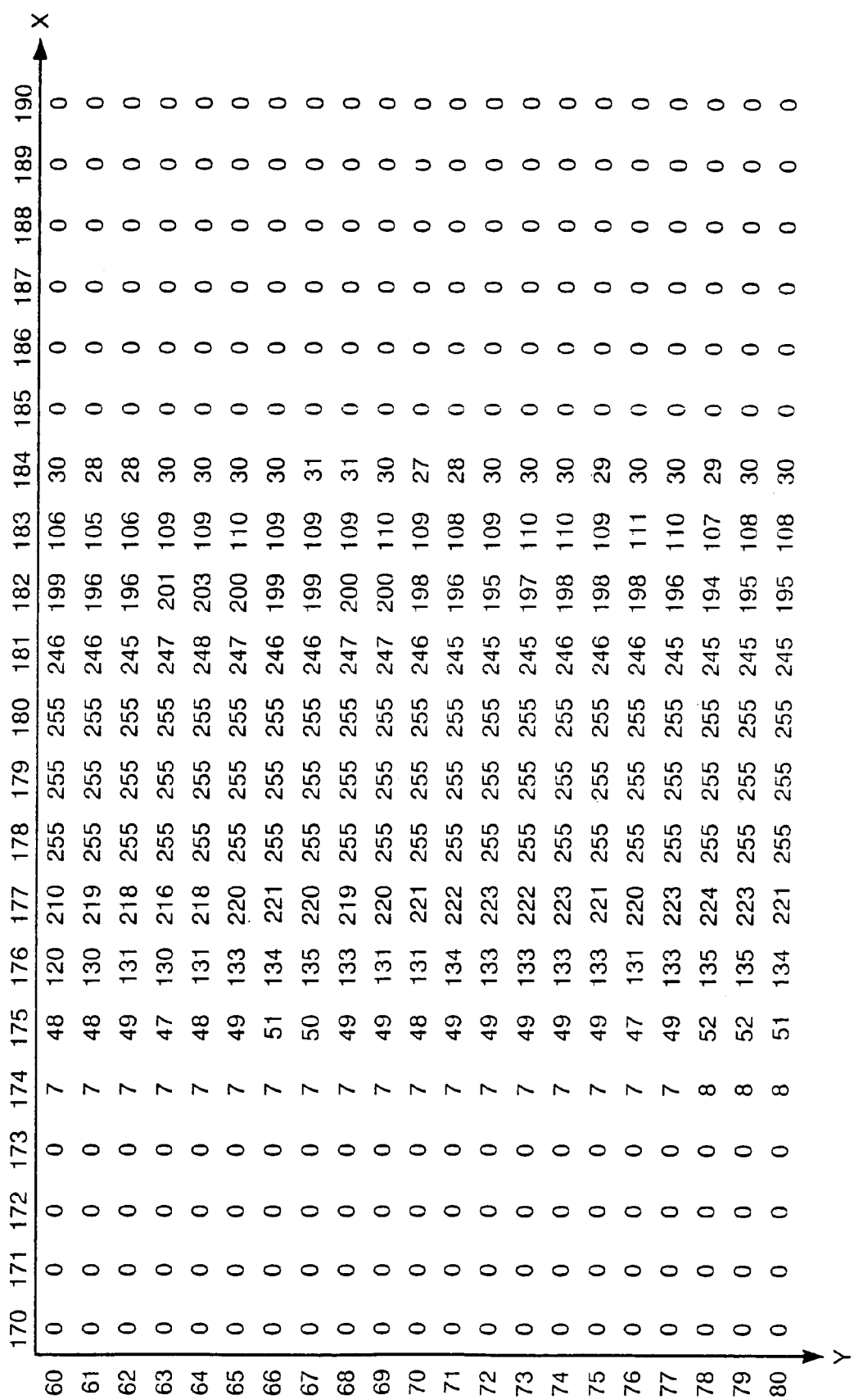
FIG. 15 is an explanatory view to show the gray level distribution in the reference image at the time of position alignment with the actual image by convolution processing of the optical point spread function in FIG. 14 and the resized reference data in FIG. 13.

It is understood that the gray level distribution of the properly resized reference image 13 as shown in FIG. 15 is quite similar to the gray level distribution of the actual pattern as shown in FIG. 12.

Figure 16:
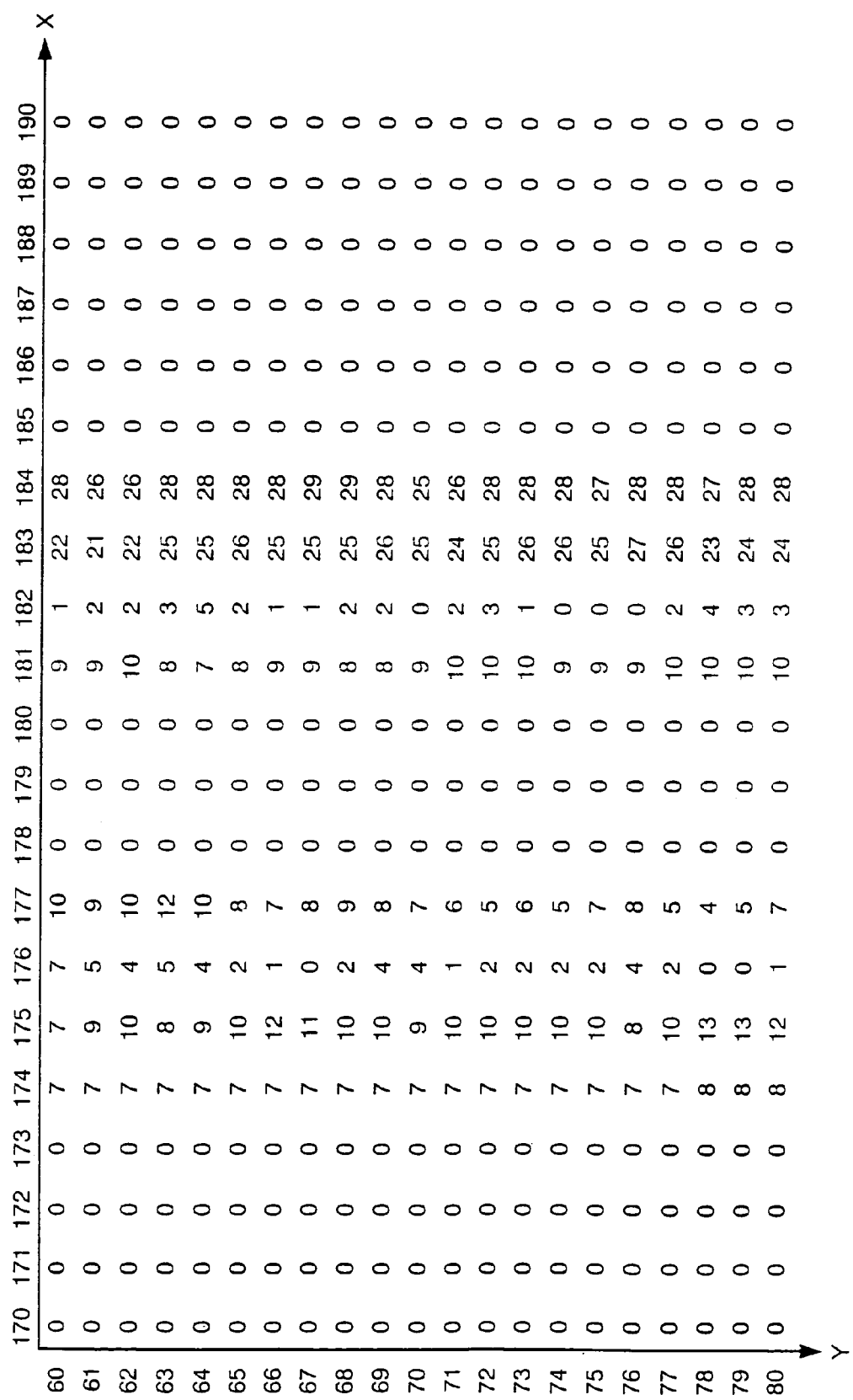
FIG. 16 is an explanatory view to show the gray level distribution for the difference between the actual image of FIG. 12 and the reference image of FIG. 15.

Further, FIG. 16 determines the difference between the actual image shown in FIG. 12 and the reference image shown in FIG. 15 for each of the corresponding pixels. As clearly understood from FIG. 16, the gray level difference between the actual image and the reference image is substantially within 30 gray levels and the reference image is prepared with an accuracy of 0.1 pixels.

Figure 17:
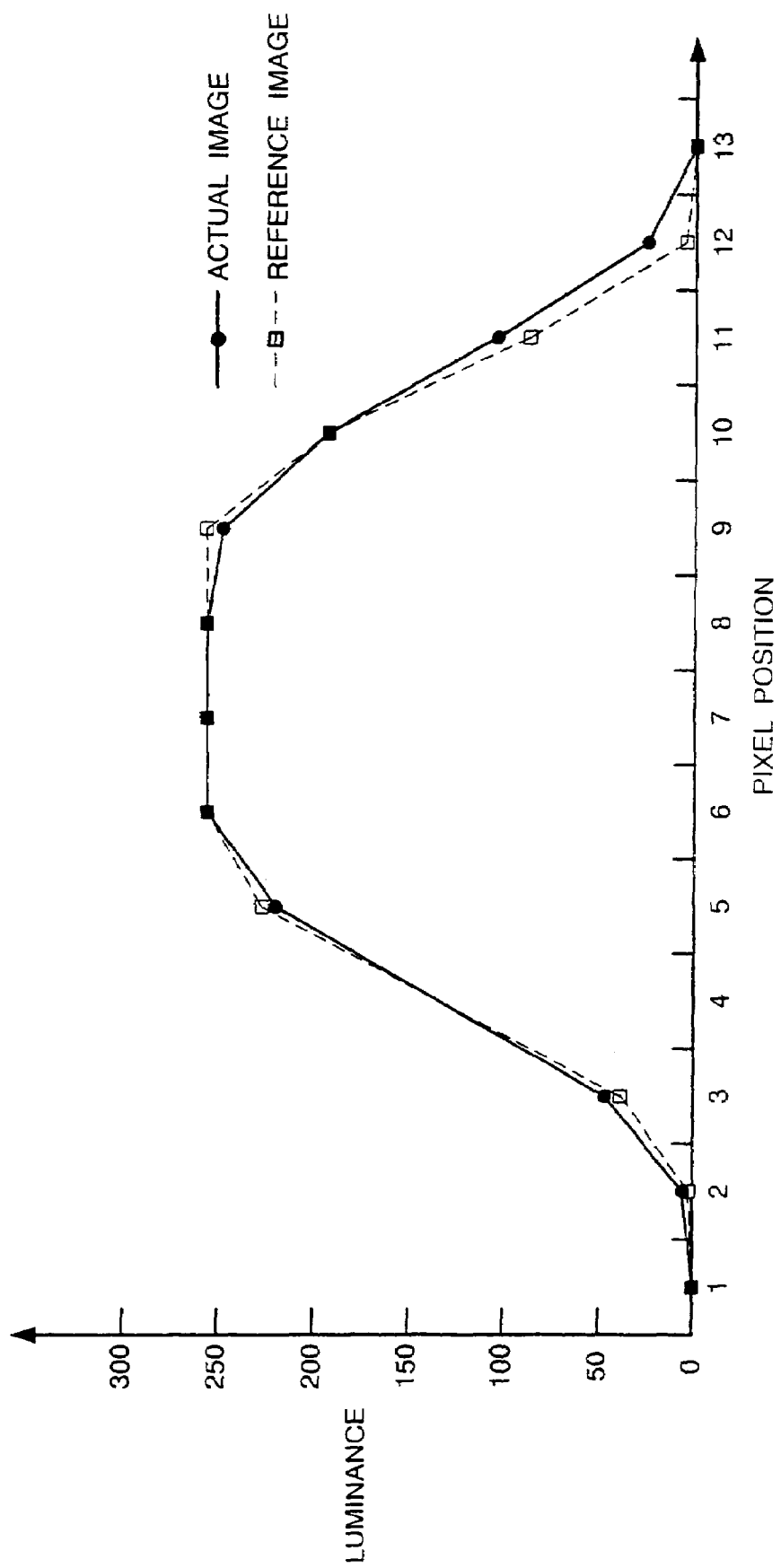
FIG. 17 is an explanatory view to show the edge profile of the reference image and the actual image.

FIG. 17 shows the edge profiles of the reference image and the actual image. It is understood that their edge distributions are quite similar.

Second Embodiment

In the pattern inspection device according to the first embodiment, the design data input section 1, the design data developing section 2, the reference image generation section 3, the photoelectric image processing section 5, the image memory 6 and the data comparison section 7 can be achieved by computer. A program to achieve the reference image preparation method according to the present invention is provided as record in the record medium such as floppy disks, CD-ROM and memory cards.

When the record medium is inserted to the auxiliary storage of the computer, the program recorded in the medium is read out. The CPU in the computer writes the read out program to the RAM or other bulk storage and, according to this program, executes the processing as explained in FIG. 2. Thus, the same operation as in the first embodiment can be achieved. By providing the reference image preparation program in the status recorded in the record medium, the operation of the pattern inspection device according to the first embodiment can be achieved on the computer, which can improve the versatility.

According to the present invention, by determining the edge boundary condition showing the gray level value corresponding to the pattern edge position from the convolution operation of the optical point spread function corresponding to the laser beam strength and the image of the inspected pattern and by detecting the edge position of the inspected pattern based on the edge boundary condition, the edge positions of the inspected pattern can be detected with an accuracy of sub-pixel unit at a speed higher than the speed in conventional operation.

Further, by providing each pixel with sub-pixels dividing a pixel to form a matrix and calculating the gray level of the pixel based on the number of sub-pixels belonging to the pattern developed in each pixel and, considering the gray level to be the width of the pattern where the count divided by the gray level step count is developed in each pixel, totaling the width of the patterns developed in each pixel, the pattern width of the inspected pattern and the pattern width of the reference data at the corresponding position can be correctly calculated at an accuracy of the sub-pixel unit.

In addition, with the gray level of each pixel calculated from the number of sub-pixels belonging to the inspected pattern and the count value obtained by dividing the gray level by the gray level step count considered to be the pattern width of the inspected pattern developed in that pixel, the pattern width of the inspected pattern is calculated. At the same time, with the gray level of each pixel calculated from the number of sub-pixels belonging to the reference data pattern and the count value obtained by dividing the gray level by the gray level step count considered to be the pattern width of the reference data developed in that pixel, the pattern width of the reference data is calculated. By calculating the pattern correction width for the reference data from the difference between the pattern width of the inspected pattern and the pattern width of the reference data, the pattern correction width (resize width) for the reference data can be determined at a high accuracy and the reference image can be generated with an accuracy of the unit of sub-pixels. Further, by the pattern edge position detection by the sub-pixel unit and the reference image generation by the sub-pixel unit, the edge position of the inspected pattern and the pattern correction width for the reference data can be calculated at a high accuracy even when the pattern corner or the pattern edge is positioned not at a break of pixels but within a pixel. This enables highly accurate preparation of the reference image similar to the image of the inspected pattern at the sub-pixel unit accuracy and the inspection sensitivity can be largely improved.

By providing the reference image preparation program in the form recorded in the record medium, the operation of the pattern inspection device can be achieved by the computer, which can improve the versatility.

Although the invention has been illustrated and described with respect to exemplary embodiment thereof, it should be understood by those skilled in the art that the foregoing and various other changes, omissions and additions may be made therein and thereto, without departing from the spirit and scope of the present invention. Therefore, the present invention should not be understood as limited to the specific embodiment set out above but to include all possible embodiments which can be embodies within a scope encompassed and equivalents thereof with respect to the feature set out in the appended claims.

What is claimed is:

1. A pattern inspection method which scans an inspected pattern formed on a substrate according to design data with a laser beam and receives light passed through said substrate with a light receiving device and, from pattern information obtained by said light receiving device, generates an image of the inspected pattern and, for coincidence between this image and reference data obtained by imaging of said design data, corrects said reference data to generate a reference image and compares the image of said inspected pattern and the reference image to detect any defects of the inspected pattern wherein, said reference image generation comprising:

provision to each pixel of sub-pixels dividing the pixel to form a matrix and calculation of a gray level of the pixel based on the number of sub-pixels belonging to a pattern developed in each pixel, calculation of a pattern width for the reference data by treating a number obtained by dividing said gray level by a gray level step count as the width of the pattern developed in that pixel, determination of an edge boundary condition showing the gray level corresponding to the pattern edge position through convolution operation of an optical point spread function corresponding to a strength of the laser beam and said inspected pattern image, detection of the edge position in said inspected pattern by the unit of sub-pixels according to said edge boundary condition, calculation of the pattern width for said inspected pattern according to the detected edge position, and calculation of the correction width of the pattern width for said reference data in the unit of sub-pixels from the difference between the pattern width of said inspected pattern and the pattern width of the reference data.

2. The reference image preparation method as set forth in claim 1 wherein the gray level of each pixel in the reference data is calculated from the number of sub-pixels belonging to said reference data pattern and, treating a count obtained by dividing this gray level by the gray level step count as the pattern width of the reference data developed in the pixel, the pattern width of the inspected pattern is calculated based on the pattern length in the unit of sub-pixels between two detected edge positions.

3. The reference image preparation method as set forth in claim 1 wherein the pattern width for said reference data is corrected by correcting the edge position of the said reference data according to the correction width.

4. A pattern inspection device comprising:

a scanning means which scans an inspected pattern formed on the substrate according to design data with a laser beam and receives light passing through said substrate with a light receiving device;

a photoelectric image processing means which generates an image of the inspected pattern from pattern information obtained by the light receiving device in said scanning means;

a reference image generation means which generates a reference image by correcting said reference data so that positions of the image of said inspected pattern and the reference data obtained by imaging of said design data coincide;

a comparison means which compares the image of said inspected pattern and the reference image to detect any defect in the inspected pattern, a first pattern width calculation means which provides each pixel with sub-pixels dividing the pixel into a matrix and calculates the gray level of each pixel based on the number of sub-pixels belonging to a pattern developed in each pixel and, with treating the count obtained by dividing this gray level by the gray level step count as the width of the pattern developed in the pixel, calculates the pattern width of the reference data;

an edge position detection means which determines an edge boundary condition showing the gray level corresponding to a pattern edge position through convolution operation of an optical point spread function corresponding to a strength of the laser beam strength and the image of said inspected pattern and detects an edge position of the inspected pattern by the unit of sub-pixels according to said edge boundary condition;

a second pattern width calculation means which calculates the pattern width of said inspected pattern according to the detected edge position; and a correction width calculation means which calculates a correction width of the pattern width for said reference data in the unit of sub-pixels from the difference between the pattern width of said inspected pattern and the pattern width of the reference data.

5. The pattern inspection device as set forth in claim 4 wherein said first pattern width calculation means calculates the gray level of each pixel in the reference data from a number of sub-pixels belonging to the pattern of said reference data and, with treating a count obtained by dividing this gray level by the gray level step count as the pattern width of the reference data developed in the pixel, and wherein said second pattern width calculation means calculates the pattern width of the inspected pattern based on the pattern length in the unit of sub-pixels between two detected edge positions.

6. The pattern inspection device as set forth in claim 4 wherein
said first pattern width calculation means
corrects the pattern width for said reference data by correcting the edge position of the reference data according to the correction width.

7. A computer readable memory storing a pattern inspection program which, by controlling the computer, scans the inspected pattern formed on the substrate according to the design data using the laser beam, receives the light passing from said substrate with the light receiving device, generates the image of the inspected pattern based on the pattern information obtained by the light receiving device and, for position coincidence between this image and the reference data obtained by imaging of said design data, corrects said reference data and generates the reference image, and compares the image of said inspected pattern and the reference image to detect defects of the inspected pattern wherein
said pattern inspection program executes,
in said reference image generation,
provision of sub-pixels dividing the pixel as a matrix to each pixel and calculation of a gray level for each pixel based on the number of sub-pixels belonging to a pattern developed in each pixel,
calculation of a pattern width for the reference data by treating a number obtained by dividing said gray level by a gray level step count as the width of the pattern developed in that pixel,
determination of an edge boundary condition showing the gray level corresponding to the pattern edge position through convolution operation of an optical point spread function corresponding to a strength of the laser beam and said inspected pattern image,
detection of the edge position of said inspected pattern by the unit of sub-pixels according to said edge boundary condition,
calculation of the pattern width for said inspected pattern according to the detected edge position, and
calculation of the correction width of the pattern width for said reference data in the unit of sub-pixels from the difference between the pattern width of said inspected pattern and the pattern width of the reference data.

8. The computer readable memory storing the pattern inspection program as set forth in claim 7 wherein
said pattern inspection program
calculates the gray level of each pixel from the number of sub-pixels belonging to the pattern of said reference data and, with treating a count obtained by dividing this gray level by the gray level step count as the pattern width of the reference data developed in the pixel, calculates the pattern width of said reference data, and
calculates the pattern width of the inspected pattern based on the pattern length in the unit of sub-pixels between two detected edge positions.

9. The computer readable memory storing the pattern inspection program as set forth in claim 7 wherein
said pattern inspection program
corrects the pattern width for said reference data by correcting the edge position of the said reference data according to the correction width.

* * * * *